United States Patent
Bonnert et al.

(10) Patent No.: US 7,709,521 B2
(45) Date of Patent: *May 4, 2010

(54) SUBSTITUTED INDOLE DERIVATIVES FOR PHARMACEUTICAL COMPOSITIONS FOR TREATING RESPIRATORY DISEASES

(75) Inventors: Roger Victor Bonnert, Loughborough (GB); Anthony Ronald Cook, Loughborough (GB); Timothy Jon Luker, Loughborough (GB); Rukhsana Tasneem Mohammed, Loughborough (GB); Stephen Thom, Loughborough (GB)

(73) Assignee: AstraZeneca AB (SE)

( * ) Notice: Subject to any disclaimer, the term of this patent is extended or adjusted under 35 U.S.C. 154(b) by 548 days.

This patent is subject to a terminal disclaimer.

(21) Appl. No.: 10/568,889

(22) PCT Filed: Aug. 16, 2004

(86) PCT No.: PCT/GB2004/003502

§ 371 (c)(1),
(2), (4) Date: Feb. 17, 2006

(87) PCT Pub. No.: WO2005/019171

PCT Pub. Date: Mar. 3, 2005

(65) Prior Publication Data

US 2006/0264444 A1    Nov. 23, 2006

(30) Foreign Application Priority Data

Aug. 18, 2003  (SE) .................................. 0302232

(51) Int. Cl.
A61K 31/404    (2006.01)
C07D 209/04    (2006.01)

(52) U.S. Cl. .................. 514/419; 548/469; 548/484; 514/415; 514/418

(58) Field of Classification Search .................. 548/469, 548/484; 514/415, 418, 419
See application file for complete search history.

(56) References Cited

U.S. PATENT DOCUMENTS

| | | | |
|---|---|---|---|
| 5,459,150 | A | 10/1995 | Brooks et al. |
| 5,486,525 | A | 1/1996 | Summers, Jr. et al. |
| 5,567,711 | A | 10/1996 | Sheppard et al. |
| 6,916,841 | B2 | 7/2005 | Seehra et al. |
| 6,933,316 | B2 | 8/2005 | Hsieh et al. |
| 7,166,607 | B2 * | 1/2007 | Bonnert et al. ......... 514/254.01 |
| 2005/0222201 | A1 | 10/2005 | Birkinshaw et al. |
| 2006/0111426 | A1 | 5/2006 | Bonnert et al. |
| 2006/0264444 | A1 | 11/2006 | Bonnert et al. |
| 2008/0027092 | A1 | 1/2008 | Bonnert et al. |
| 2008/0051586 | A1 | 2/2008 | Keegan et al. |
| 2008/0249110 | A1 | 10/2008 | Bonnert et al. |

| | | |
|---|---|---|
| 2009/0143449 | A1 | 6/2009 Bonnert et al. |

FOREIGN PATENT DOCUMENTS

| | | |
|---|---|---|
| EP | 0254241 | 1/1988 |
| EP | 0530907 A1 | 3/1993 |
| EP | 0576347 A1 | 12/1993 |
| EP | 0924209 B1 | 6/1999 |
| EP | 1170594 | 1/2002 |
| EP | 1505061 | 2/2005 |
| GB | 1 356 834 | 6/1974 |
| GB | 2422831 | 8/2006 |
| WO | WO94/19321 | 9/1994 |
| WO | WO95/16687 | 6/1995 |
| WO | WO98/13368 | 4/1998 |
| WO | WO99/09007 | 2/1999 |
| WO | WO00/78761 A1 | 12/2000 |
| WO | WO 01/32621 | 5/2001 |
| WO | WO01/47922 A2 | 7/2001 |
| WO | WO 01/92224 A1 | 12/2001 |
| WO | WO 03/064387 A2 | 8/2003 |
| WO | WO 03/066046 | 8/2003 |
| WO | WO 03/066047 | 8/2003 |
| WO | WO03/097598 | 11/2003 |
| WO | WO 03/101961 A1 | 12/2003 |
| WO | WO 03/101981 | 12/2003 |
| WO | WO 2004/007451 A1 | 1/2004 |
| WO | WO 2004/016609 A1 | 2/2004 |
| WO | WO2004/106302 | 12/2004 |
| WO | WO 2005/019171 | 3/2005 |
| WO | WO 2005/040114 | 5/2005 |
| WO | WO 2005/054232 | 6/2005 |
| WO | WO2006/075139 | 7/2006 |
| WO | WO 2007/138282 | 12/2007 |
| WO | WO 2007/140786 | 12/2007 |
| WO | WO 2008/000409 | 1/2008 |

OTHER PUBLICATIONS

Database CA 'Online! Chemical Abstracts Service, Columbus, Ohio, US; Tanimoto, Norihiko et al: "Preparation of indole derivatives as PGD2 receptor antagonists" XP002301963 retrieved from STN Data accession No. 2003:931327.

(Continued)

Primary Examiner—Golam M M Shameem
(74) Attorney, Agent, or Firm—Fish & Richardson P.C.

(57) ABSTRACT

The present invention relates to substituted indoles of formula (I) useful as pharmaceutical compounds for treating respiratory disorders.

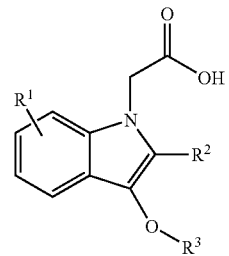

(I)

11 Claims, No Drawings

OTHER PUBLICATIONS

Vippagunta, Sudha R. et al., "Crystalline Solids", *Advanced Drug Delivery Reviews*, vol. 48, pp. 3-26, (2001).
Atkinson et al., "A New Synthesis of 3-Arylthioindoles", *Synthesis* 6:480-481 (1988).
Cecil Textbook of Medicine, 20th edition, vol. 2:1992-1996 (1996).
Cecil Textbook of Medicine, 20$^{th}$ edition, vol. 2:2050-2057 (1996).
FDA mulls drug to slow late-stage Alzheimer's [online], [retrieved on Sep. 23, 2003]. Retrieved from the Internet, URL:http://www.cnn.com/2003/HEALTH/conditions/09/24/alzheimers.drug.ap/indexhtml>.
Garcia et al., "A Novel Synthesis of 3-Cyanoindoles and a New Route to Indole-3-Carboxylic Acid Derivatives", *Tetrahedron Letters* 26(15):1827-1830 (1985).
Hamel et al., "Regioselective Synthesis of Mixed Indole 2,3-Bis-(sulfides). A Study of the Mechanism of the Second Sulfenylation of Indole", *J. Org. Chem.* 61:1573-1577 (1996).
Hary et al., "Efficient synthesis of 3-(4,5-dihydro-1*H*-imidazole-2-yl)-1*H*-indoles", *Tetrahedron Letters* 42:5187-5189 (2001).
Howard et al., "Synthesis and aldose reductase inhibitory activity of substituted 2(1*H*)-benzimidazolone- and oxindole-1-acetic acids", *Eur J Med Chem* 27:779-789 (1992).
Lüscher et al., "Deblocking of *o*-Nitrophenylsulfenyl-Protected Peptides by Ammonium Thiocyanate and (2-Methyl-1-indolyl) acetic acid", *Helv. Chim. Acta* 66(2):602-605 (1983).
Matassa et al., "Evolution of a Series of Peptidoleukotriene Antagonists: Synthesis and Structure/Activty Relationships of 1,3,5-Substituted Indoles and Indazoles", *J. Med. Chem.* 33:1781-1790 (1990).
Matsugi et al., "An efficient sylfenylation of aromatics using highly active quinone mono *O,S*-acetal bearing a pentafluorophenylthio group", *Tetrahedron Letters* 42:1077-1080 (2001).
Matsugi et al., "Facile and Efficient Sulfenylation Method Using Quinone Mono-*O,S*-Acetals under Mild Conditions", *J. Org. Chem.* 66:2434-2441 (2001).
Ovenden et al., "Echinosulfonic Acids A-C and Echinosulfone A: Novel Bromoindole Sulfonic Acids and a Sulfone from a Southern Australian Marine Sponge, *Echinodictyum*", *J. Nat. Prod.* 62:1246-1249 (1999).
STN International, CAPLUS accession No. 1977:535057, Document No. 87:135057, Sankyo Co., Ltd., "3-Indolyl thio ethers", & JP,A2,52039671, 19770328, RN 64137-76-4, 54491-43-9, 56366-45-1.
STN International, CAPLUS accession No. 1980:6356, Document No. 92:6356, Gabrielyan, G.E. et al.: "Indole derivatives. LX. Synthesis of indole compounds with a furan ring", & Armyanskii Khimicheskii Zhurnal (1979), 32(4), 309-14, RN 51842-57-0.
STN International, CAPLUS accession No. 2001:235566, Document No. 134:266203, Kato, Susumu et al.: "Preparation and application of benzopyranone derivatives"; & JP,A2,2001089471, 20010403, RN 332082-10-7.
STN International, CAPLUS accession No. 2001:338492, Document No. 134:353315, Wakunaga Pharmaceutical Co., Ltd., "Preparation of indole derivatives as chymase inhibitors and drugs containing the same as the active ingredient", & WO,A1,2001032621, 20010510, RN 64137-76-4, 336186-33-5.
STN International, CHEMCATS accession No. 2000:1027702, Apr. 26, 2001, 8004-3013, "1H-Indole-1-acetic acid, 2-methyl-3-(phenylthio)-, ethyl ester", CAS Registry No. 300860-50-8.
STN International, file CAPLUS, CAPUS accession No. 1995:401159, Document No. 122:187576, Yoshitomi Pharmaceutical Industries, Ltd., "Preparation of fused pyrazole derivatives", & JP,A2, 06206872, 19940726.
Morissette et al., "High-throughput crystallization: polymorphs, salts, co-crystals and solvates of pharmaceutical solids", *Advanced Drug Delivery Reviews* 56:275-300 (2004).
Patani and LaVoie, "Bioisosterism: A Rational Approach in Drug Design", *Chem Rev*. 96:3147-3176 (1996).
"COPD: Causes and Prevention." NIH SeniorHealth. National Heart, Lung, and Blood Institute. Accessed Apr. 6, 2009. <http://nihseniorhealth.gov/copd/causesandprevention/01.html>.
"Prevention of Cystic Fibrosis." WrongDiagnosis.com. Accessed Apr. 6, 2009. <http://www.wongdiagnosis.com/c/cf/prevent.htm>.

* cited by examiner

SUBSTITUTED INDOLE DERIVATIVES FOR PHARMACEUTICAL COMPOSITIONS FOR TREATING RESPIRATORY DISEASES

CROSS-REFERENCE TO RELATED APPLICATIONS

This application is a national phase application under 35 U.S.C. § 371 of PCT International Application No. PCT/GB2004/003502, filed Aug. 16, 2004, which claims priority to Swedish Application Serial No. 0302232-4, filed Aug. 18, 2003.

The present invention relates to substituted indoles useful as pharmaceutical compounds for treating respiratory disorders, pharmaceutical compositions containing them, and processes for their preparation.

EPA 1 170 594 discloses methods for the identification of compounds useful for the treatment of disease states mediated by prostaglandin D2, a ligand for orphan receptor CRTh2. GB 1356834 discloses a series of compounds said to possess anti-inflammatory, analgesic and antipyretic activity. It has now surprisingly been found that certain indole acetic acids are active at the CRTh2 receptor, and as a consequence are expected to be potentially useful for the treatment of various respiratory diseases, including asthma and COPD.

In a first aspect the invention therefore provides a compound of formula (I) or a pharmaceutically acceptable salt or solvate thereof:

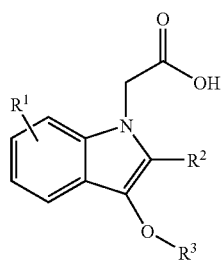

(I)

in which $R^1$ is one or more substituents selected from hydrogen, halogen, CN, nitro, $SO_2R^4$, OH, $OR^4$, $S(O)xR^4$, $SO_2NR^5R^6$, $CONR^5R^6$, $NR^5R^6$, $NR^9SO_2R^4$, $NR^9SO_2NR^5R^6$, $NR^9CO_2R^4$, $NR^9COR^4$, aryl, heteroaryl, $C_2$-$C_6$ alkenyl, $C_2$-$C_6$ alkynyl or $C_{1-6}$ alkyl the latter five groups being optionally substituted by one or more substituents independently selected from halogen, CN, $NR^9SO_2R^4$, $NR^9CO_2R^4$, $NR^9COR^4$, $OR^8$ and $NR^5R^6$, $S(O)_xR^7$ where x is 0, 1 or 2;

$R^2$ is hydrogen, halogen, CN, $SO_2R^4$ or $CONR^5R^6$, $CH_2OH$, $CH_2OR^4$ or $C_{1-7}$alkyl, the latter group being optionally substituted by one or more substituents independently selected from halogen atoms, $OR^8$ and $NR^5R^6$, $S(O)_xR^7$ where x is 0, 1 or 2;

$R^3$ is aryl or heteroaryl each of which is optionally substituted by one or more substituents independently selected from hydrogen, halogen, CN, nitro, OH, $SO_2R^4$, $OR^4$, $SR^4$, $SOR^4$, $SO_2NR^5R^6$, $CONR^5R^6$, $NR^5R^6$, $NHSO_2R^4$, $NHCO_2R^4$, $NHCOR^4$, $NR^7SO_2R^4$, $NR^7CO_2R^4$, $NR^7COR^4$, $NHC_{1-6}alkylNR^5R^6$, $C_2$-$C_6$ alkenyl, $C_2$-$C_6$ alkynyl, $C_{1-6}$ alkyl, the latter three groups being optionally substituted by one or more substituents independently selected from halogen atoms, CN, $OR^8$ and $NR^5R^6$, $S(O)_xR^7$ where x=0, 1 or 2;

$R^4$ represents aryl, heteroaryl, or $C_{1-6}$alkyl all of which may be optionally substituted by one or more substituents independently selected from halogen atoms, aryl, heteroaryl, $OR^{10}$, OH, $NR^{11}R^{12}$, $S(O)_xR^{13}$ (where x=0, 1 or 2), $CONR^{14}R^{15}$, $NR^{14}COR^{15}$, $SO_2NR^{14}R^{15}$, $NR^{14}SO_2R^{15}$, CN, nitro;

$R^5$ and $R^6$ independently represent a hydrogen atom, a $C_{1-6}$alkyl group, or an aryl, or a heteroaryl, the latter three of which may be optionally substituted by one or more substituents independently selected from halogen atoms, aryl, $OR^8$ and $NR^{14}R^{15}$, $CONR^{14}R^{15}$, $NR^{14}COR^{15}$, $SO_2NR^{14}R^{15}$, $NR^{14}SO_2R^{15}$; CN, nitro or $R^5$ and $R^6$ together with the nitrogen atom to which they are attached can form a 3-8 membered saturated heterocylic ring optionally containing one or more atoms selected from O, $S(O)_x$ where x=0, 1 or 2, $NR^{16}$, and itself optionally substituted by $C_{1-3}$ alkyl;

$R^7$ and $R^{13}$ independently represent a $C_1$-$C_6$, alkyl, an aryl or a heteroaryl group, all of which may be optionally substituted by halogen atoms;

$R^8$ represents a hydrogen atom, $C(O)R^9$, $C_1$-$C_6$ alkyl (optionally substituted by halogen atoms or aryl) an aryl or a heteroaryl group (optionally substituted by halogen);

each of $R^9$, $R^{10}$, $R^{11}$, $R^{12}$, $R^{14}$, $R^{15}$, independently represents a hydrogen atom, $C_1$-$C_6$ alkyl, an aryl or a heteroaryl group (all of which may be optionally substituted by halogen atoms); and $R^{16}$ is hydrogen, $C_{1-4}$ alkyl, —$COC_1$-$C_4$ alkyl, $COYC_1$-$C_4$alkyl where Y is O or $NR^7$.

In the context of the present specification, unless otherwise indicated, an alkyl or alkenyl group or an alkyl or alkenyl moiety in a substituent group may be linear, branched or cyclic.

Aryl is phenyl or naphthyl.

Heteroaryl as used herein is defined as a 5-7 membered aromatic ring or can be a 6,6- or 6,5-fused bicyclic group, both the mono- and bi-cyclic rings containing one or more heteroatoms selected from N, S and O. Examples include pyridine, pyrimidinie, thiazole, oxazole, pyrazole, imidazole, furan, isoxazole, pyrrole, isothiazole and azulene, naphthyl, indene, quinoline, isoquinoline, indole, indolizine, benzo[b]furan, benzo[b]thiophene, 1H-indazole, benzimidazole, benzthiazole, 1,2benzisothiazole, benzoxazole, purine, 4H-quinolizine, cinnoline, phthalazine, quinazoline, quinoxaline, 1,8-naphthyridine, pteridine and quinolone.

Heterocyclic rings as defined for $R^5$ and $R^6$ means saturated heterocycles, examples include morpholine, thiomorpholine, azetidine, imidazolidine, pyrrolidine, piperidine and piperazine.

The term alkyl, whether alone or as part of another group, includes straight chain, branched or cyclic alkyl groups.

Preferably $R^1$ is hydrogen, halogen, heteroaryl, $CF_3$, alkyl, cyano, $CONR^5R^6$, $SO_2NR^5R^6$, $SO_2$alkyl, $NR^9SO_2R^4$, $NR^9COR^4$, $NR^9SO_2NR^5R^6$. More preferably $R^1$ is hydrogen, chlorine, fluorine, $NHSO_2Me$, $NHSO_2Et$, $SO_2Me$, $CF_3$, NHCOMe, pyrazinyl, or $NHSO_2NMe_2$.

The $R^1$ group can be present at any suitable position on the indole ring, preferably the $R^1$ group is present at the 4 or 5-position.

Preferably $R^2$ is $C_{1-6}$alkyl, more preferably methyl.

Suitably $R^3$ is phenyl or heteroaryl. Suitable heteroaryl groups includes a 6,6- or 6,5-fused bicyclic aromatic ring systems optionally containing one to three heteroatoms selected from nitrogen, oxygen or sulphur, or a 5- to 7-membered heterocyclic ring containing one to three heteroatoms selected from nitrogen, oxygen or sulphur as described above. When $R^3$ is a heterocycle, heteroatom(s) can be present at any position in the ring.

The substituent can be present on any suitable position of the aryl or heteroaryl ring.

Preferably $R^3$ is phenyl substituted by halogen atoms, $CONR^5R^6$, $SO_2NR^5R^6$, cyano or $SO_2R^4$ groups. The substituent(s) may be present on any position of the phenyl ring. More preferably the substituents are chlorine or $SO_2$alkyl, $CONHC_{1-6}$ alkyl (where the alkyl group maybe linear or branched and optionally substituted by $NR^5R^6$, $SO_2NR^5R^6$) or $R^3$ is cyano. Most preferably the substituents are chlorine or $SO_2Me$, CONHMe, CONHEt, CONHPr, $NH(CH_2)_3NH_2$ or cyano. Preferably the substituent is present at the 4-position of the phenyl ring.

Preferred compounds of the invention include:
3-(4-Chlorophenoxy)-5-fluoro-2-methyl-1H-indole-1-acetic acid;
5-Fluoro-2-methyl-3-[4-(methylsulfonyl)phenoxy]-1H-indole-1-acetic acid;
3-(4-Chlorophenoxy)-2-methyl-4-[(methylsulfonyl)amino]-1H-indole-1-acetic acid;
4-(Acetylamino)-3-(4-chlorophenoxy)-2-methyl-1H-indole-1-acetic acid;
3-(4-chlorophenoxy)-2-methyl-5-(methylsulfonyl)-1H-indole-1-acetic acid;
3-(4-chlorophenoxy)-2-methyl-5-(trifluoromethyl)-1H-indole-1-acetic acid;
3-(4-Chlorophenoxy)-2-methyl-5-[(methylsulfonyl)amino]-1H-indole-1-acetic acid;
3-(4-Chlorophenoxy)-5-[(ethylsulfonyl)amino]-2-methyl-1H-indole-1-acetic acid;
3-(4-Carboxyphenoxy)-5-fluoro-2-methyl-1H-indole-1-acetic acid;
5-Fluoro-2-methyl-3-[4-[(methylamino)carbonyl]phenoxy]-1H-indole-1-acetic acid;
3-[4-[(Ethylamino)carbonyl]phenoxy]-5-fluoro-2-methyl 1H-indole-1-acetic acid;
5-Fluoro-2-methyl-3-[4-[[(1-methylethyl)amino]carbonyl]phenoxy]-1H-indole-1-acetic acid;
3-(4-Carboxyphenoxy)-5-chloro-2-methyl-1H-indole-1-acetic acid;
5-Fluoro-3-[4-(methoxycarbonyl)phenoxy]-2-methyl-1H-indole-1-acetic acid;
5-Chloro-3-[4-(methoxycarbonyl)phenoxy]-2-methyl-1H-indole-1-acetic acid;
5-Chloro-2-methyl-3-[4-[(methylamino)carbonyl]phenoxy]-1H-indole-1-acetic acid;
5-Chloro-3-[4-[(ethylamino)carbonyl]phenoxy]-2-methyl-1H-indole-1-acetic acid;
Sodium 5-Chloro-2-methyl-3-[4-[[(1-methylethyl)amino]carbonyl]phenoxy]-1H-indole-1-acetate;
3-[4-[[(2-Aminoethyl)amino]carbonyl]phenoxy]-5-fluoro-2-methyl-1H-indole-1-acetic acid;
2,5-Dimethyl-3-[4-(methylsulfonyl)phenoxy]-1H-indole-1-acetic acid;
2-Methyl-3-[4-(methylsulfonyl)phenoxy]-5-(trifluoromethyl)-1H-indole-1-acetic acid;
5-Chloro-α,2-dimethyl-3-[4-(methylsulfonyl)phenoxy]-1H-indole-1-acetic acid;
5-Cyano-2-methyl-3-[4-(methylsulfonyl)phenoxy]-1H-indole-1-acetic acid;
3-(4-Chlorophenoxy)-4-[(ethylsulfonyl)amino]-2-methyl 1H-indole-1-acetic acid;
3-(4-Chlorophenoxy)-4-[[(dimethylamino)sulfonyl]amino]-2-methyl-1H-indole-1-acetic acid;
3-(4-Chlorophenoxy)-2-methyl-4-pyrazinyl-1H-indole-1-acetic acid;
3-(4-Chlorophenoxy)-2-methyl-4-[[(1-methylethyl)sulfonyl]amino]-1H-indole-1-acetic acid;
3-[4-[(Dimethylamino)sulfonyl]phenoxy]-5-fluoro-2-methyl-1H-indole-1-acetic acid;
3-[4-(Ethylsulfonyl)phenoxy]-5-fluoro-2-methyl-1H-indole-1-acetic acid;
3-[4-(Ethylsulfonyl)phenoxy]-2-methyl-5-(trifluoromethyl)-1H-indole-1-acetic acid;
3-(4Cyanophenoxy)-2-methyl-5-(trifluoromethyl)-1H-indole-1-acetic acid;
3-(4-Cyanophenoxy)-5-fluoro-2-methyl 1H-indole-1-acetic acid;

and pharmaceutically acceptable salts thereof.

Certain compounds of formula (I) are capable of existing in stereo isomeric forms. It will be understood that the invention encompasses all geometric and optical isomers of the compounds of formula (I) and mixtures thereof including racemates. Tautomers and mixtures thereof also form an aspect of the present invention.

The compound of formula (I) above may be converted to a pharmaceutically acceptable salt or solvate thereof, preferably a basic addition salt such as ammonium, sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate. Preferred salts include sodium and ammonium salts.

In a second aspect the invention provides a compound of formula (IA) or a pharmaceutically acceptable salt or solvate thereof, the compounds of formula (IA) being a sub-set of compounds of formula (I) above:

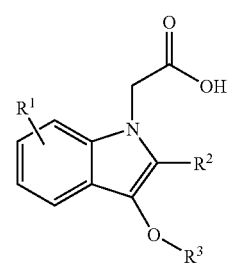

(I)

in which $R^1$ is one or more substituents selected from hydrogen, halogen, CN, nitro, $SO_2R^4$, OH, $OR^4$, $S(O)xR^4$, $SO_2NR^5R^6$, $CONR^5R^6$, $NR^5R^6$, $NR^9SO_2R^4$, $NR^9CO_2R^4$, $NR^9COR^4$, aryl, heteroaryl, $C_2$-$C_6$ alkenyl, $C_2$-$C_6$ alkynyl or $C_1$-$C_6$ alkyl, the latter five groups being optionally substituted by one or more substituents independently selected from halogen, CN, $NR^9SO_2R^4$, $NR^9CO_2R^4$, $NR^9COR^4$, $OR^8$ and $NR^5R^6$, $S(O)_xR^7$ where x is 0, 1 or 2;

$R^2$ is hydrogen, halogen, CN, $SO_2R^4$ or $CONR^5R^6$, $CH_2OH$, $CH_2OR^4$ or $C_{1-7}$alkyl, the latter group being optionally substituted by one or more substituents independently selected from halogen atoms, $OR^8$ and $NR^5R^6$, $S(O)_xR^7$ where x is 0, 1 or 2;

$R^3$ is aryl or heteroaryl each of which is optionally substituted by one or more substituents independently selected from hydrogen, halogen, CN, nitro, OH, $SO_2R^4$, $OR^4$, $SR^4$, SOR$^4$, SO$_2$NR$^5$R$^6$, CONR$^5$R$^6$, NR$^5$R$^6$, NHSO$_2$R$^4$, NHCO$_2$R$^4$, NHCOR$^4$, NR$^7$SO$_2$R$^4$, NR$^7$CO$_2$R$^4$, NR$^7$COR$^4$, C$_2$-C$_6$ alkenyl, C$_2$-C$_6$ alkynyl, C$_{1-6}$ alkyl, the latter three groups being optionally substituted by one or more substituents independently selected from halogen atoms, CN, OR$^8$ and NR$^5$R$^6$, S(O)$_x$R$^7$ where x=0, 1 or 2;

R$^4$ represents aryl, heteroaryl, or C$_{1-6}$alkyl all of which may be optionally substituted by one or more substituents independently selected from halogen atoms, aryl, heteroaryl, OR$^{10}$, OH, NR$^{11}$R$^{12}$, S(O)$_x$R$^{13}$ (where x=0, 1 or 2), CONR$^{14}$R$^{15}$, NR$^{14}$COR$^{15}$, SO$_2$NR$^{14}$R$^{15}$, NR$^{14}$SO$_2$R$^{15}$, CN, nitro;

R$^5$ and R$^6$ independently represent a hydrogen atom, a C$_{1-6}$alkyl group, or an aryl, or a heteroaryl, the latter three of which may be optionally substituted by one or more substituents independently selected from halogen atoms, aryl, OR$^8$ and NR$^{14}$R$^{15}$, CONR$^{14}$R$^{15}$, NR$^{14}$COR$^{15}$, SO$_2$NR$^{14}$R$^{15}$, NR$^{14}$SO$_2$R$^{15}$; CN, nitro or R$^5$ and R$^6$ together with the nitrogen atom to which they are attached can form a 3-8 membered saturated heterocylic ring optionally containing one or more atoms selected from O, S(O)$_x$ where x=0, 1 or 2, NR$^{16}$, and itself optionally substituted by C$_{1-3}$ alkyl;

R$^7$ and R$^{13}$ independently represent a C$_1$-C$_6$, alkyl, an aryl or a heteroaryl group, all of which may be optionally substituted by halogen atoms;

R$^8$ represents a hydrogen atom, C(O)R$^9$, C$_1$-C$_6$ alkyl (optionally substituted by halogen atoms or aryl) an aryl or a heteroaryl group (optionally substituted by halogen);

each of R$^9$, R$^{10}$, R$^{11}$, R$^{12}$, R$^{14}$, R$^{15}$, independently represents a hydrogen atom, C$_1$-C$_6$ alkyl, an aryl or a heteroaryl group (all of which may be optionally substituted by halogen atoms); and R$^{16}$ is hydrogen, C$_{1-4}$ alkyl, —COC$_1$-C$_4$ alkyl, COYC$_1$-C$_4$alkyl where Y is O or NR$^7$.

In a further aspect the invention provides a process for the preparation of a compound of formula (I) which comprises reaction of a compound of formula (II):

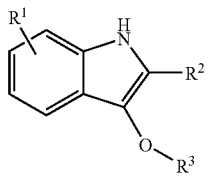

(II)

in which R$^1$, R$^2$ and R$^3$ are as defined in formula (I) or are protected derivatives thereof, with a compound of formula (IIA):

L-CH$_2$CO$_2$R$^{17}$    (IIA)

where R$^{17}$ is an ester forming group and L is a leaving group in the presence of a base, and optionally thereafter in any order:

removing any protecting group
 hydrolysing the ester group R$^{17}$ to the corresponding acid
 forming a pharmaceutically acceptable salt or solvate.

The reaction can be carried out in suitable solvents such as THF or DMF using a base such as sodium hydride, potassium carbonate or the like. Suitable groups R$^{17}$ include C$_{1-6}$ alkyl groups such as methyl, ethyl or tertiary-butyl. Suitable L is a leaving group such as halo, in particular bromo. Preferably the compound of formula (IIA) is ethyl, methyl or tertiary-butyl bromoacetate.

Hydrolysis of the ester group R$^{17}$ can be carried out using routine procedures, for example by stirring with aqueous sodium hydroxide or trifluoroacetic acid.

It will be appreciated that certain functional groups may need to be protected using standard protecting groups. The protection and deprotection of functional groups is for example, described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

Compounds of formula (II) can be prepared by reacting a compound of formula (III) with a compound of formula (IV):

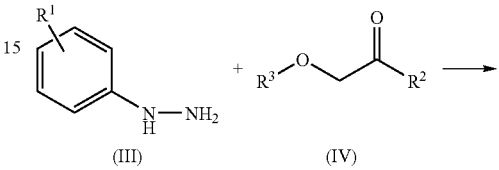

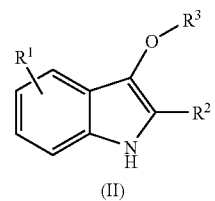

(II)

in which R$^1$, R$^2$ and R$^3$ are as defined in formula (I).

Preferably the reaction is carried out in a suitable solvent such as ethanol and then dichloromethane or THF with PCl$_3$ with heating or at room temperature.

Or, the reaction can be carried out in acetic acid.

Compounds of formulae (III), (IV) and (V) are commercially available or can be prepared using standard chemistry well known in the art.

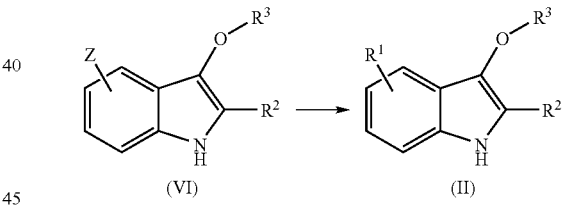

Compounds of formula (II) in which R$^1$ is NR$^9$SO$_2$R$^4$ or NR$^9$COR$^4$, can be prepared from compounds of formula (VI) in which W is an amino group. The group W is reacted with a suitable acetyl or sulfonyl chloride in the presence of a base such as triethylamine.

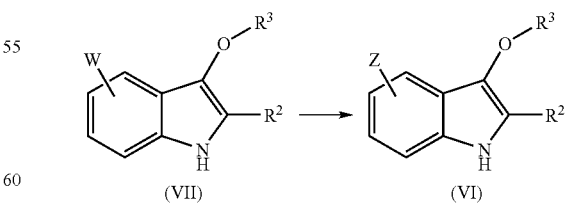

Compounds of formula (VI) are prepared from compounds of formula (VII) in which Z is a nitro group. The compounds of formula (VII) are treated with hydrogen in a suitable solvent such as methanol, in the presence of an appropriate catalyst such as platinum on charcoal.

Compounds of formula (VII) are prepared from compounds of formula (III) and (IV) as outlined above.

Certain compounds of formula (II), (VI), (VII) and (IV) are believed to be novel and form a further aspect of the invention.

In a further aspect, the present invention provides the use of a compound of formula (I), a prodrug, pharmaceutically acceptable salt or solvate thereof for use in therapy.

The compounds of formula (I) have activity as pharmaceuticals, in particular as modulators of CRTh2 receptor activity, and may be used in the treatment (therapeutic or prophylactic) of conditions/diseases in human and non-human animals which are exacerbated or caused by excessive or unregulated production of $PGD_2$ and its metabolites. Examples of such conditions/diseases include:

A compound of the invention, or a pharmaceutically acceptable salt thereof, can be used in the treatment of:

(1) (respiratory tract)—obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

(2) (bone and joints) arthritides associated with or including osteoarthritis/osteoarthrosis, both primary and secondary to e.g. congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthiopatlhy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies.

(3) (skin) psoriasis, atopic dermatitis, contact dermatitis or other eczematous dermatoses, and delayed-type hypersensitivity reactions; phyto- and photodennatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis;cutaneous lymphonlas, non-melanomna skin cancer and other dysplastic lesions; drug-induced disorders including fixed drug eruptions.

(4) (eyes) blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial.

(5) (gastrointestinal tract) glossitis, gingivitis, periodontitis; oesophagitis, including reflux; eosinophilic gastroenteritis, mastocytosis, Crohn's disease, colitis including ulcerative colitis, proctitis, piluritis ani; coeliac disease, irritable bowel syndrome, and food-related allergies which may have effects remote from the gut (for example migraine, rhinitis or eczema).

(6) (abdominal) hepatitis, including autoimmune, alcoholic and viral; fibrosis and cirrhosis of the liver; cholecystitis; pancreatitis, both acute and chronic.

(7) (genitourinary) nephritis including interstitial and glomeruloneplritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female).

(8) (Allograft rejection) acute and chronic following, for example, transplantation of kidney, heart, liver, lung, bone marrow, skin or cornea or following blood transfusion; or chronic graft versus host disease;

(9) (CNS) Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes.

(10) Other auto-immune and alleraic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome.

(11) Other disorders with an inflammatory or immunological component; including acquired immune deficiency syndrome (AIDS), leprosy, Sezary syndrome, and paraneoplastic syndromes.

(12) (Cardiovascular); atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (e.g. syphilitic); vasculitides; disorders of the proximal and peripheral veins including phlebitis and thrombosis, including deep vein thrombosis and complications of varicose veins.

(13) (Oncology) treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

(14) Diseases associated with raised levels of $PGD_2$ or its metabolites. Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CRTh2 receptor subfamily.

Particular conditions which can be treated with the compounds of the invention are asthma, rhinitis and other diseases in which raised levels of $PGD_2$ or its metabolites. It is preferred that the compounds of the invention are used to treat asthma.

In a further aspect, the present invention provides the use of a compound of formula (I), or a pharmaceutically acceptable salt or solvate thereof, as hereinbefore defined in the manufacture of a medicament for use in therapy.

The invention further relates to combination therapies wherein a compound of formula (1) or a pharmaceutically acceptable salts, solvate or in vivo hydrolysable ester thereof, or a pharmaceutical composition or formulation comprising a compound of formula (1) is administered concurrently or sequentially with therapy and/or an agent for the treatment of any one of asthma, allergic rhinitis, cancer, COPD, rheumatoid arthritis, psoriasis, inflammatory bowel diseases, osteoarthritis or osteoporosis.

In particular, for the treatment of the inflammatory diseases rheumatoid arthritis, psoriasis, inflammatory bowel disease, COPD, asthma and allergic rhinitis the compounds of the invention may be combined with agents such as TNF-α inhibitors such as anti-TNF monoclonal antibodies (such as Remicade, CDP-870 and D.sub2.E.sub7.) and TNF receptor immunioglobulin molecules (such as Enbrel.reg.), non-selective COX-1/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin), COX-2 inhibitors (such as meloxicam, celecoxib, rofecoxib, valdecoxib and etoricoxib) low dose methotrexate, lefunomide; ciclesonide; hydroxychloroquine, d-penicillamine, auranofin or parenteral or oral gold.

The present invention still further relates to the combination of a compound of the invention together with a leukotriene biosynthesis inhibitor, 5-lipoxygenase (5-LO) inhibitor or 5-lipoxygenase activating protein (FLAP) antagonist such as zileuton; ABT-761; fenleuton; tepoxalin; Abbott-79175; Abbott-85761; N-(5-substituted)-thiophene-2-alkylsulfonaniides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY x 1005.

The present invention still further relates to the combination of a compound of the invention together with a receptor antagonist for leukotrienes LTB.sub4., LTC.sub4., LTD.sub4., and LTE.sub4. selected from the group consisting of the phenothiazin-3-ones such as L-651,392; amidino compounds such as CGS-25019c; benzoxalamines such as ontazolast; benzenecarboximidaniides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention together with a PDE4 inhibitor including inhibitors of the isoform PDE4D.

The present invention still further relates to the combination of a compound of the invention together with a antihistaminic H.sub 1. receptor antagonists such as cetirizine, loratadine, desloratadine, fexofenadine, astemizole, azelastine, and chlorpheniramine.

The present invention still further relates to the combination of a compound of the invention together with a gastroprotective H.sub2. receptor antagonist.

The present invention still further relates to the combination of a compound of the invention together with an α.sub1.- and α.sub2.-adrenoceptor agonist vasoconstrictor sympathomimetic agent, such as propylhexedrine, phenylephrine, phenylpropaniolamine, pseudoephedrine, naphazoline hydrochloride, oxymetazoline hydrochloride, tetrahydrozoline hydrochloride, xylometazoline hydrochloride, and ethylnorepineplrine hydrochloride.

The present invention still further relates to the combination of a compound of the invention together with anticholinergic agents such as ipratropium bromide; tiotropium bromide; oxitropium bromide; pirenzepine; and telenzepine.

The present invention still further relates to the combination of a compound of the invention together with a β.sub1.- to β.sub4.-adrenoceptor agonists such as metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the invention together with an insulin-like growth factor type I (IGF-1) mimetic.

The present invention still further relates to the combination of a compound of the invention together with an inhaled glucocorticoid with reduced systemic side effects, such as prednisone, prednisolone, flunisolide, triamcinolone acetonide, beclomethasone dipropionate, budesonide, fluticasone propionate, and mometasone furoate.

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-12.

The present invention still further relates to the combination of a compound of the invention together with other modulators of chemokine receptor function such as CCR1, CCR2, CCR2A, CCR2-B, CCR3, CCR4, CCR5, CCR6, CCR7, CCR8, CCR9, CCR10 and CCR11 (for the C-C family); CXCR1, CXCR2, CXCR3, CXCR4 and CXCR5 (for the C—X—C family) and $CX_3CR1$ for the C—$X_3$—C family.

The present invention still further relates to the combination of a compound of the invention together with antiviral agents such as Viracept, AZT, aciclovir and famciclovir, and antisepsis compounds such as Valant.

The present invention still further relates to the combination of a compound of the invention together with cardiovascular agents such as calcium channel blockers, lipid lowering agents such as statins, fibrates, beta-blockers, Ace inhibitors, Angiotensin-2 receptor antagonists and platelet aggregation inhibitors.

The present invention still further relates to the combination of a compound of the invention together with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metryfonate.

The present invention still further relates to the combination of a compound of the invention together with (i) tryptase inhibitors; (ii) platelet activating factor (PAF) antagonists; (iii) interleukin converting enzyme (ICE) inhibitors; (iv) IMPDH inhibitors; (v) adhesion molecule inhibitors including VLA-4 antagonists; (vi) cathepsins; (vii) MAP kinase inhibitors; (viii) glucose-6 phosphate dehydrogenase inhibitors; (ix) kinin-$B_1$- and $B_2$-receptor antagonists; (x) anti-gout agents, e.g., colchicine; (xi) xanthine oxidase inhibitors, e.g., allopurinol; (xii) uricosuric agents, e.g., probenecid, sulfinpyrazone, and benzbromarone; (xiii) growth hormone secretagogues; (xiv) transforming growth factor (TGFβ); (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) Tachykinin $NK_1$. and $NK_3$. receptor antagonists selected from the group consisting of NKP-608C; SB-233412 (talnetant); and D-4418; (xx) elastase inhibitors selected from the group consisting of UT-77 and ZD-0892; (xxi) TNFα converting enzyme inhibitors (TACE); (xxii) induced nitric oxide synthase inhibitors (iNOS) or (xxiii) chemoattractant receptor-homologous molecule expressed on TH2 cells, (CRTH2 antagonists).

The compounds of the present invention may also be used in combination with osteoporosis agents such as roloxifene, droloxifene, lasofoxifene or fosomax and immunosuppressant agents such as FK-506, rapamycin, cyclosporine, azathioprine, and methotrexate;

The compounds of the invention may also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc and P2X7 receptor antagonists.

The compounds of the invention can also be used in combination with existing therapeutic agents for the treatment of cancer. Suitable agents to be used in combination include:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel (Taxol®); antitumour antibiotics (for example anthracyclines like adriamycin, bleomycin, doxorubicin, daunomycin, epirubicin, idaiubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the aiiti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO99/02166, WO00/40529, WO00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of CRTh2 receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating diseases mediated by PGD2 or its metabolites wherein the prostanoid binds to its receptor (especially CRTh2) receptor, which comprises administering to a patient a therapeutically effective amount of a compound of formula (I), or a pharmaceutically acceptable salt, solvate or prodrug thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

For the above-mentioned therapeutic uses the dosage administered will, of course, vary with the compound employed, the mode of administration, the treatment desired and the disorder indicated.

The compound of formula (I), prodrugs and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as herein before defined, in association with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compound of the invention is administered orally.

The present invention also provides a pharmaceutical composition comprising a compound of formula (I), or a pharmaceutically acceptable salt or solvate thereof, as herein before defined, in association with a pharmaceutically acceptable adjuvant, diluent or carrier.

The invention will now be illustrated by the following non-limiting examples in which, unless stated otherwise:

(i) the title and sub-titled compounds of the examples and methods were named using the ACD labs/name program (version 6.0) from Advanced Chemical Development Inc, Canada;

(ii) unless stated otherwise, reverse phase preparative HPLC was conducted using a Symmetry, NovaPak or Ex-Teira reverse phase silica column;

(iii) Flash column chromatography refers to normal phase silica chromatography (iv) solvents were dried with $MgSO_4$ or $Na_2SO_4$ (v) Evaporations were carried out by rotary evaporation in vacuo and work-up procedures were carried out after removal of residual solids such as drying agents by filtration;

(vi) Unless otherwise stated, operations were carried out at ambient temperature, that is in the range 18-25° C. and under an atmosphere of an inert gas such as argon or nitrogen;

(vii) yields are given for illustration only and are not necessarily the maximum attainable;

(viii) the structures of the end-products of the formula (1) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(ix) intermediates were not generally fully characterised and purity was assessed by thin layer chromatography (TLC), high-performance liquid chromatography (HPLC), mass spectrometry (MS), infra-red (IR) or NMR analysis;

(x) mass spectra (MS): generally only ions which indicate the parent mass are reported when given, $^1$H NMR data is quoted in the form of delta values for major diagnostic protons, given in parts per million (ppm) relative to tetramethylsilane (TMS) as an internal standard;

(xi) the following abbreviations are used:

dec decomposed

DMF N,N-Dimethyl formamide

EtOAc Ethylacetate h hour

NMP N-methylpyrrolidine

RT ROOM TEMPERATURE

TFA trifluoroacetic acid

THF tetrahydrofuran

EXAMPLES

Example 1

3-(4-Chlorophenoxy)-5-fluoro-2-methyl-1H-indole-1-acetic acid (i) 3-(4-Chlorophenoxy)-5-fluoro-2-methyl-1H-indole 1-(4-Chloro-phenoxy)-propan-2-one (2.05 g) was added to a stirred solution of (4-fluoro-phenyl)-hydrazine (1.4 g) in ethanol (30 ml) at RT. After 2 h, the solvent was removed under reduced pressure and the residue dissolved in DCM (30 ml). Phosphorus trichloride (1.06 ml) was added dropwise to the solution and after stirring at RT for 16 h the reaction was quenched with aq. sodium hydrogencarbonate solution. The mixture was extracted with DCM, the organics washed with water, dried and evaporated under reduced pressure. The residue was purified by chromatography on silica eluting with 20% ethylacetate/iso-hexane. Yield 0.75 g MS: ESI (–ve): 274/6 (M–1)

(ii) 3-(4-Chlorophenoxy)-5-fluoro-2-methyl-1H-indole-1-acetic acid, ethyl ester

Sodium hydride (60% disp. in oil) (0.12 g) was added portionwise to a stirred solution of the product from step (i) (0.75 g) in DMF (10 ml) at RT. After 10 min, ethylbromoacetate (345 ul) was added, the mixture stirred at RT for 3 h then quenched with water and extracted with diethylether. The organics were washed with water, dried and evaporated under reduced pressure. The residue was purified by chromatography on silica eluting with 15% ethylacetate/iso-hexane. Yield 0.38 g MS: APCI (–ve): 360/2 (M–1)

(iii) 3-(4-Chlorophenoxy)-5-fluoro-2-methyl-1H-indole-1-acetic acid

A solution of 2M sodium hydroxide (3 ml) was added to a stirred mixture of the product from step (ii) (0.36 g), water (10 ml) and THF (10 ml). After 2 h the solution was acidified with 2M hydrochloric acid and extracted with diethylether. The organics were washed with water, dried and evaporated under reduced pressure. The residue was recrystallised from diethylether/isohexane. Yield 138 mg $^1$H NMR DMSO-d6: δ 13.10 (1H, s); 7.51 (1H, dd); 7.37-7.33 (2H, m); 6.98-6.83 (4H, m); 5.02 (2H, s); 2.19 (3H, s). MS: APCI (–ve): 332/4 (M–1) Mpt. 198° C.

Example 2

5-Fluoro-2-methyl-3-[4-(methylsulfonyl)phenoxy]-1H-indole-1-acetic acid (i) 1-[4-(Methylthio)phenoxy]-2-propanone A mixture of chloroacetone (10 ml), potassium carbonate (21 g), and 4-(methylthio)phenol (10 g) in acetone (200 ml) was heated under reflux for 6 h. The solvent was removed under reduced pressure and the residue partitioned between diethylether/water. The organics were separated, dried and evaporated under reduced pressure. The residue was purified by chromatography on silica eluting with 5-10% ethylacetate/iso-hexane. Yield 12.43 g $^1$H NMR CDCl$_3$: δ 7.26 (2H, d); 6.83 (2H, d); 4.52 (2H, s); 2.45 (3H, s); 2.28 (3H, s)

(ii) 5-Fluoro-2-methyl-3-[4-(methylthio)phenoxy]-1H-indole

A mixture of the product from step (i) (3.63 g) and 4-fluorohydrazine hydrochloride (2 g) in acetic acid (40 ml) were heated at 90° C. for 2 h, cooled, and the solvent removed under reduced pressure. The residue was partitioned between diethylether/water, the organics were separated, washed with aq sodium hydroxide solution, water, dried and evaporated under reduced pressure. The residue was purified by chromatography on silica eluting with 10% ethylacetate/iso-hexane. Yield 0.34 g MS: ESI (–ve): 286 (M–1)

(iii) 5-Fluoro-2-methyl-3-[4-(methylthio)phenoxy]-1H-indole-1-acetic acid, ethyl ester A mixture of the product from step (ii) (335 mg), potassium carbonate (0.3 g) and ethyl bromoacetate (0.16 ml) in DMF (5 ml) was stirred at RT. After 16 h, ethyl bromoacetate (0.1 ml) and potassium carbonate (0.15 g) were added and the mixture heated at 50° C. for 4 h then partitioned between diethylether/water. The organics were washed with water, dried and evaporated under reduced pressure. The residue was purified by chromatography on silica eluting with 10% ethylacetate/iso-hexane. Yield 0.41 g MS: ESI (–ve): 372 (M–1)

(iv) 5-Fluoro-2-methyl-3-[4-(methylsulfonyl)phenoxy]-1H-indole-1-acetic acid, ethyl ester 3-Chloroperoxybenzoic acid (0.6 g) was added to a solution of the product from step (iii) (0.4 g) in DCM (10 ml) at RT. After 2.5 h the mixture was partitioned between DCM/aq. sodium metabisulphite solution, the organics washed with aq. sodium hydrogencarbonate solution, water, dried and evaporated under reduced pressure. The residue was purified by chromatography on silica eluting with 30% ethylacetate/iso-hexane. Yield 0.2 g (v) 5-Fluoro-2-methyl-3-[4-(methylsulfonyl)phenoxy]-1H-indole-1-acetic acid The title compound was prepared by the method of example 1 step (iii) using the product from step (iv). Yield 0.075 g $^1$H NMR DMSO-d6: δ 13.12 (1H, s); 7.88 (2H, d); 7.54 (1H, dd); 7.10 (2H, d); 7.01-6.96 (1H, m); 6.91-6.88 (1H, m); 5.05 (2H, s); 3.18 (3H, s); 2.2 (3H, s) MS: APCI (–ve): 376 (M–1) Mpt. 204-7° C.

Example 3

3-(4-Chlorophenoxy)-2-methyl-4-[(methylsulfonyl)amino]-1H-indole-1-acetic acid (i) (2-Bromo-5-nitrophenyl)-hydrazine To 2-bromo-5-nitro-aniline (5 g) in conc hydrochloric acid (50 ml) at 0° C. was added a solution of sodium nitrite (1.45 g) in water (20 ml). After 1 h, a solution of tin dichloride (8.73 g) in conc hydrochloric acid (15 ml) was added. The reaction was stirred for 30 min at 0° C. and 1 h at room temperature. The resulting solid was filtered off and recrystalised from hot ethanol. Yield 2.9 g.

$^1$H NMR DMSO-d6: δ 7.92 (1H, d); 7.88 (1H, d); 7.71 (1H, dd)

(ii) 7-Bromo-3-(4-chlorophenoxy)-2-methyl-4-nitro-1H-indole

A mixture of the compound from (i) (2.4 g) and 1-(4-Chloro-phenoxy)-propan-2-one (1.65 g) in MeCN (20 ml) and water (5 ml) was stirred for 16 h. The volatiles were removed in vacuo. AcOH (50 ml) was added and the reaction heated at 75° C. for 72 h. The volatiles were evaporated under reduced pressure and the residue was purified by chromatography on silica eluting with 5% ethylacetate/iso-hexane. Yield 0.34 g $^1$HNMR CDCl$_3$: δ 7.92 (1H, d); 8.43 (1H, s); 7.82 (1H, d), 7.39 (1H, d), 7.19 (2H, d), 6.79 (1H, d), 2.40 (3H, s)

(iii) 7-Bromo-3-(4-chlorophenoxy)-2-methyl-4-nitro-1H-indole-1-acetic acid 1,1 dimethylethyl ester Sodium hydride (60% disp. in oil) (0.043 g) was added to a stirred solution of the product from step (ii) (0.34 g) in THF (4 ml) at RT. After 1 h, tert-butylbromoacetate (170 ul) was added, the mixture stirred at RT for 16 h then quenched with water and extracted with diethylether. The organics were dried and evaporated under reduced pressure. The residue was purified by chromatography on silica eluting with 10% diethylether/iso-hexane. Yield 0.192 g $^1$H NMR CDCl$_3$: δ 7.63 (1H, d), 7.38 (1H, d), 7.19 (2H, d), 6.78 (2H, d), 5.29 (2H, s), 2.26 (3H, s), 1.48 (9H, s)

(iv) 4-Amino-3-(4-chlorophenoxy)-2-methyl-1H-indole-1-acetic acid, 1,1-dimethylethyl ester To a solution of the product from step (iii) (0.18 g) in EtOAc (30 ml) was added triethylamine (0.15 ml) and 5% Pt/C (36 mg) and the reaction stirred under hydrogen (1 atm) for 2 h. The reaction was filtered through celite and the filtrate evaporated under reduced pressure. Yield 0.139 g.

$^1$H NMR CDCl$_3$: δ 7.21 (2H, d), 6.97 (1H, t), 6.91 (2H, d), 6.62 (1H, d), 6.27 (1H, d), 4.62 (2H, s), 3.94 (2H, bs), 2.15 (3H, s), 1.44 (9H, s)

(v) 3-(4-Chlorophenoxy)-2-methyl-4-[(methylsulfonyl)amino]-1H-indole-1-acetic acid, 1,1-dimethylethyl ester To a solution of the product from step (iv) (70 mg) in MeCN (1 ml) was added triethylamine (50 ul) and methanesulfonyl chloride (24 ul) and the reaction stirred at 50° C. for 3 h. The residue was partitioned between diethylether/water, the organics were separated, washed with aq potassium hydrogensulfate solution, brine, dried and evaporated under reduced pressure. The residue was purified by chromatography on silica eluting with 5-30% ethylacetate/iso-hexane.

Yield 42 mg $^1$H NMR CDCl$_3$: δ 7.28-7.23 (3H, m), 7.16 (1H, t), 7.04 (1H, d), 6.91 (2H, d), 6.84 (1H, s), 4.69 (2H, s), 2.66 (3H, s), 2.20 (3H, s), 1.46 (9H, s)

(vi) 3-(4-Chlorophenoxy)-2-methyl-4-[(methylsulfonyl)amino]-1H-indole-1-acetic acid A solution of 1M sodium hydroxide (0.5 ml) was added to a stirred mixture of the product from step (v) (40 mg) in THF (1 ml). After 3 h, further 1M sodium hydroxide (1 ml) was added and the reaction heated at 55° C. for 16 h. Water (10 ml) was added and the THF evaporated under reduced pressure. The solution was acidified with 2M hydrochloric acid and the resulting solid filtered off and dried. Yield 24 mg $^1$H NMR DMSO-d6: δ 8.54 (1H, s), 7.37-7.32 (3H, m), 7.08 (1H, t), 6.93 (1H, d), 6.87 (2H, d), 4.99 (2H, s), 2.70 (3H, s), 2.13 (3H, s) MS: APCI (−ve): 407 (M−1)

Example 4

4-(Acetylamino)-3-(4-chlorophenoxy)-2-methyl-1H-indole-1-acetic acid

(i) 4-(Acetylamino)-3-(4-chlorophenoxy)-2-methyl-1H-indole-1-acetic acid, 1,1-dimethylethyl ester To a solution of the product from example 3 step (iv) (70 mg) in MeCN (1 ml) was added triethylamine (50 μl) and acetyl chloride (17 μl) and the reaction stirred at 50° C. for 3 h. The residue was partitioned between diethylether/water, the organics were separated, washed with aq potassium hydrogensulfate solution, brine, dried and evaporated under reduced pressure. The residue was purified by chromatography on silica eluting with 5-30% ethylacetate/iso-hexane.

Yield 51 mg $^1$H NMR CDCl$_3$: δ 7.90 (1H, d), 7.89 (1H, s), 7.24 (2H, d), 7.16 (1H, t), 6.97 (1H, d), 6.91 (2H, d), 4.67 (2H, s), 2.18 (3H, s), 1.89 (3H, s), 1.43 (9H, s)

(ii) 4-(Acetylamino)-3-(4-chlorophenoxy)-2-methyl-1H-indole-1-acetic acid

The title compound was prepared by the method of example 3 step (vi) using the product from step (i). Yield 0.035 g $^1$H NMR DMSO-d6: δ 9.01 (1H, s), 7.32 (2H, d), 7.26 (2H, d), 7.05 (2H, m), 6.84 (2H, d), 5.00 (2H, s), 2.16 (3H, s), 1.67 (3H, s) MS: APCI (−ve): 371 (M−1)

Example 5

3-(4-chlorophenoxy)-2-methyl-5-(methylsulfonyl)-1H-indole-1-acetic acid

(i) 3-(4-chlorophenoxy)-2-methyl-5-(methylthio)-1H-indole 1-(4-Chloro-phenoxy)-propan-2-one (2.66 g) was added to a stirred solution of [4-(methylthio)phenyl]-hydrazine hydrochloride (2.5 g) in MeCN (15 ml)/HCl (0.5M, 15 ml) at RT. The reaction was stirred at 50° C. for 1 h. After cooling to room temperature, the reaction was partitioned between ethylacetate/water, the organics were separated, washed with aq sodium hydroxide (1 M), dried and evaporated under reduced pressure. The residue was purified by chromatography on silica eluting with 5-20% ethylacetate/iso-hexane. The resulting hydrazone was dissolved in THF (80 ml). Sodium bicarbonate solid (1.04 g) was added followed by phosphorus trichloride (0.41 ml) dropwise, and the reaction stirred at RT for 2 h. Further phosphorus trichloride (1.20 ml) was added dropwise, and the reaction stirred at RT for 16 h. The reaction was quenched with water. The mixture was extracted with ethylacetate, the organics washed with aq. sodium hydrogencarbonate, brine, dried and evaporated under reduced pressure. The residue was purified by chromatography on silica eluting with 5-10% ethylacetate/iso-hexane. Yield 0.45 g.

$^1$H NMR DMSO-d6: δ 11.09 (1H, s), 7.39 (2H, d), 7.34 (1H, d), 7.10 (1H, dd), 7.06 (1H, s), 6.97 (2H, d), 2.44 (3H, s), 2.29 (3H, s).

(ii) 3-(4-chlorophenoxy)-2-methyl-5-(methylthio)-1H-indole-1-acetic acid, methyl ester A mixture of the product from step (i) (0.45 g), potassium carbonate (0.415 g) and methyl bromoacetate (0.21 ml) in DMF (3 ml) was stirred at 50° C. for 3 h. The reaction was partitioned between ethylacetate/water. The organics were washed with water, dried and evaporated under reduced pressure. The residue was purified by chromatography on silica eluting with 5-15% ethylacetate/iso-hexane. Yield 0.33 g $^1$H NMR DMSO-d6: δ 7.46 (1H, d), 7.36 (2H, d), 7.10 (1H, dd), 7.03 (1H, d), 6.91 (2H, d), 5.14 (2H, s), 3.70 (3H, s), 2.39 (3H, s), 2.17 (3H, s).

(iii) 3-(4-chlorophenoxy)-2-methyl-5-(methylsulfonyl)-1H-indole-1-acetic acid, methyl ester To the product from step (ii) (0.32 g) in acetone (4 ml) and water (4 ml) was added solid sodium bicarbonate (0.57 g) followed by oxone (0.69 g in water (2.5 ml)) and the reaction was stirred for 3 h. The reaction was quenched with sodium bisulfite and partitioned between ethylacetate/water. The organics were dried and evaporated under reduced pressure. The residue was purified by chromatography on silica eluting with 30-60% ethylacetate/iso-hexane.

Yield 0.24 g $^1$H NMR DMSO-d6: δ 7.78 (1H, d), 7.67 (2H, m), 7.38 (2H, d), 6.94 (2H, d), 5.28 (2H, s), 3.72 (3H, s), 3.15 (3H, s), 2.24 (3H, s).

(iv) 3-(4-Chlorophenoxy)-2-methyl-5-(methylsulfonyl)-1H-indole-1-acetic acid

A solution of 1M sodium hydroxide (1 ml) was added to a stirred mixture of the product from step (iii) (235 mg) in THF (1 ml). After 2 h, water (10 ml) was added and the solution extracted with DCM. The solution was acidified with 2 M hydrochloric acid and extracted with ethylacetate. These later organics were dried and evaporated under reduced pressure. Yield 135 mg $^1$H NMR DMSO-d6: δ 7.79 (1H, d), 7.68 (1H, s), 7.65 (1H, d), 7.37 (2H, d), 6.94 (2H, d), 5.15 (2H, s), 3.15 (3H, s), 2.25 (3H, s). MS: APCI (−ve): 411 (M+NH4−1)

Example 6

3-(4-chlorophenoxy)-2-methyl-5-(trifluoromethyl)-1H-indole-1-acetic acid (i) 3-(4-Chlorophenoxy)-2-methyl-5-(trifluoromethyl)-1H-indole 1-(4-Chloro-phenoxy)-propan-2-one (1.05 g) was added to a stirred solution of (4-trifluoromethyl-phenyl)-hydrazine (1 g) in methanol (8 ml) at RT. After 16 h, the solvent was removed under reduced pressure and the residue triturated with iso-hexane to give a hydrazone as a beige solid. This was dissolved in THF (60 ml). Sodium bicarbonate solid (1.43 g) was added followed by phosphorus trichloride (1.26 ml) dropwise, and the reaction stirred at RT for 16 h. The reaction was quenched with aq. sodium hydrogencarbonate solution (100 ml). The mixture was extracted with ethylacetate, the organics washed with sodium hydrogencarbonate solution, brine, dried and evaporated under reduced pressure. The residue was purified by recrystalisation from diethylether/iso-hexane. Yield 1 g $^1$H NMR DMSO-d6: δ 11.51 (1H, s), 7.52 (1H, d), 7.38 (2H, m), 7.35 (2H, d), 6.93 (2H, d), 2.28 (3H, s).

(ii) 3-(4-Chlorophenoxy)-2-methyl-5-(trifluoromethyl)-1H-indole-1-acetic acid, methyl ester A mixture of the product from step (i) (0.60 g), potassium carbonate (0.516 g) and methyl bromoacetate (0.26 ml) in DMF (4 ml) was stirred at 50° C. for 4 h. The reaction was partitioned between ethylacetate/water. The organics were washed with water, dried and evaporated under reduced pressure. The residue was purified by chromatography on silica eluting with 10-20% ethylacetate/iso-hexane. Yield 0.44 g $^1$H NMR DMSO-d6: δ 7.74 (1H, d), 7.40 (2H, m), 7.37 (2H, d), 6.93 (2H, d), 5.26 (2H, s), 3.72 (3H, s), 2.23 (3H, s).

(iii) 3-(4-chlorophenoxy)-2-methyl-5-(trifluoromethyl)-1H-indole-1-acetic acid

The title compound was prepared by the method of example 5 step (iv) using the product from step (ii). Yield 0.27 g $^1$H NMR DMSO-d6: δ 13.18 (1H, s), 7.74 (1H, d), 7.43 (2H, m), 7.37 (2H, d), 6.93 (2H, d), 5.12 (2H, s), 2.23 (3H, s). MS: APCI (−ve): 382 (M−1).

Example 7

3-(4-Chlorophenoxy)-2-methyl-5-[(methylsulfonyl)amino]-1H-indole-1-acetic acid (i) 3-(4-Chlorophenoxy)-2-methyl-5-nitro-1H-indole-1-acetic acid, methyl ester 1-(4-Chloro-phenoxy)-propan-2-one (3.62 g) was added to a stirred solution of (4-nitro-phenyl)-hydrazine (3 g) in methanol (125 ml)/DCM (100 ml) at RT. After 16 h, the solvent was removed under reduced pressure to give a hydrazone as a yellow solid. This was dissolved in THF (200 ml). Sodium bicarbonate solid (9.88 g) was added followed by phosphorus trichloride (5.22 ml) dropwise, and the reaction stirred at RT for 10 min and then heated at 60° C. for 16 h. After cooling to RT, the bulk of the solvent was removed, and the reaction quenched with water. The mixture was extracted with ethylacetate, the organics dried and evaporated under reduced pressure. The residue was dissolved in DCM, filtered through Celite, and evaporated under reduced pressure to give 3-(4-chlorophenoxy)-2-methyl-5-nitro-1H-indole as a beige solid. This was reacted with methyl bromoacetate by the method of example 6 step (ii) to give the crude sub-titled product. This was purified by chromatography on silica eluting with 30-40% ethylacetate/iso-hexane. Yield 2.39 g.

$^1$H NMR DMSO-d6: δ 8.02 (1H, s), 7.94 (1H, d), 7.39 (2H, d), 6.97 (2H, d), 6.60 (1H, s), 5.31 (2H, s), 3.73 (3H, s), 2.25 (3H, s).

(ii) 5-Amino-3-(4-chlorophenoxy)-2-methyl-1H-indole-1-acetic acid, methyl ester

The sub title compound was prepared by the method of example 3 step (iv) using the product from step (i). Yield 2.18 g $^1$H NMR DMSO-d6: δ 7.34 (2H, d), 7.11 (1H, d), 6.90 (2H, d), 6.46 (1H, dd), 6.26 (1H, d), 4.98 (2H, s), 4.42 (2H,s), 3.68 (3H, s), 2.12 (3H, s).

(iii) 3-(4-Chlorophenoxy)-2-methyl-5-[(methylsulfonyl)amino]-1H-indole-1-acetic acid To a solution of the product from step (ii) (0.688 g) in MeCN (5 ml) was added triethylamine (1.39 ml) and methanesulfonyl chloride (0.54 ml) and the reaction stirred at rt for 5 h. Further triethylamine (0.83 ml) and methanesulfonyl chloride (0.54 ml) were added and the reaction stirred for 16 h. The residue was partitioned between ethylacetate/water, the organics were separated, washed with 2M hydrochloric acid, sodium hydrogencarbonate solution, brine, dried and evaporated under reduced pressure. The residue was purified by chromatography on silica eluting with 30-40% ethylacetate/iso-hexane to give a mixture of mono- and di-methanesulfonamides. This was dissolved in THF (2 ml) and a solution of 1 M sodium hydroxide (4 ml) was added and the reaction heated at 55° C. for 2 h. After cooling to RT, water (10 ml) was added and the solution extracted with ethylacetate. The aqueous solution was acidified with 2M hydrochloric acid and extracted with ethylacetate. These later organics were dried and evaporated under reduced pressure. Yield 302 mg
$^1$H NMR DMSO-d6: δ 13.07 (1H, s), 9.26 (1H, s), 7.46 (1H, d), 7.35 (2H, d), 7.02 (1H, dd), 6.99 (1H, s), 6.91 (2H, d), 5.00 (2H, s), 2.82 (3H, s), 2.18 (3H, s). MS: APCI (−ve): 407 (M−1).

Example 8

3-(4-Chlorophenoxy)-5-[(ethylsulfonyl)amino]-2-methyl-1H-indole-1-acetic acid The title compound was prepared by the method of example 7 step (iii) using ethanesulfonyl chloride and the product from example 7 step (ii). Yield 155 mg
$^1$H NMR DMSO-δ6: δ 13.08 (1H, s), 9.36 (1H, s), 7.44 (1H, d), 7.35 (2H, d), 7.01 (1H, dd), 6.97 (1H, d), 6.91 (2H, d), 4.98 (2H, s), 2.90 (2H, q), 2.18 (3H, s), 1.13 (3H, t). MS: APCI (−ve): 421 (M−1).

Example 9

3-(4-Carboxyphenoxy)-5-fluoro-2-methyl-1H-indole-1-acetic acid

(i) Methyl 4-[[(2Z)-2-[(4-fluorophenyl)hydrazono]propyl]oxy]-benzoate

Methyl 4-(2-oxopropoxy)benzoate (6.21 g) was added to a solution of 4-fluorophenylhydrazine (2.88 g) in ethanol (50 ml). After 1.5 h the precipitate was collected, washed with ethanol and isohexane and dried to give the sub-title compound (3.72 g).
MS: ESI (+ve): 317 [M+H]$^+$100%

(ii) Methyl 4-[(5-fluoro-2-methyl-1H-indol-3-yl)oxy]-benzoate

Phosphorus trichloride (0.7 ml) was added to a solution of the product from step a) (3.72 g) in THF (120 ml) and the mixture was stirred for 3 days. Aq sodium bicarbonate was added and the mixture was extracted with ethyl acetate. The organic extracts were dried (MgSO$_4$), evaporated and purified by chromatography (silica, petrol—ether and petrol—ethyl acetate as eluents) to give the sub-title compound (2.17 g).
MS: ESI (+ve and −ve): 300 [M+H]$^+$100% and 298 [M−H]$^-$100%

(iii) 1,1-Dimethylethyl 5-fluoro-3-[4-(methoxycarbonyl)phenoxy]-2-methyl-1H-indole-1-acetate Potassium tert-butoxide (8.1 ml of 1 M solution in THF) was added to a solution of the product from step b) (2.24 g) and tert-butyl bromoacetate in THF (10 ml) at 0° C. Further potassium tert-butoxide (4 ml) was added after 1 h and stirred for a further 1 h. Aq ammonium chloride was added and the mixture was extracted with ethyl acetate. The organic extracts were dried (MgSO$_4$), evaporated and purified by chromatography (silica, petrol—ether as eluent) to give the sub-title compound (2.41 g).
MS: ESI (−ve): 412 [M−H]$^-$100%

(iv) 3-(4-Carboxyphenoxy)-5-fluoro-2-methyl-1H-indole-1-acetic acid

A solution of the product from step c) (2.41 g) and lithium hydroxide (517 mg) in THF (15 ml), methanol (4 ml) and water (4 ml) was stirred for 30 h. The mixture was acidified with 2M HCl and the mixture was extracted with ethyl acetate. The organic extracts were dried (MgSO$_4$), and evaporated to give a solid. Crystallisation from iso-hexane—acetone gave the title compound as an off-white solid (1.51 g). M.p 227-8° C.
$^1$H NMR DMSO-d6: δ 12.91 (2H, s), 7.91 (2H, d), 7.52 (1H, dd), 7.00-6.93 (3H, m), 6.86 (1H, dd), 5.04 (2H, s) 2.20 (3H, s). MS: ESI (+ve): 341 [M+H]$^+$100%

Example 10

5-Fluoro-2-methyl-3-[4-[(methylamino)carbonyl]phenoxy]-1H-indole-1-acetic acid

(i) Methyl 5-Fluoro-2-methyl-3-[4-[(methylamino)carbonyl]phenoxy]-1H-indole-1-acetate HATU (294 mg) was added to a solution of the product from Example 9 (208 mg) and Hunig's base (0.3 ml) in NMP (1.2 ml). After 10 min a solution of methylamine in THF (0.4 ml, 2M) was added and stirred for 20 h. 2M HCl (1 ml) was added and the mixture was extracted with ethyl acetate. The organic extracts were dried (MgSO$_4$), evaporated, re-dissolved in methanol and treated with a solution of trimethylsilyldiazomethan (1 ml, 2M in ether). Evaporation and purification by chromatography (silica, petrol—acetone as eluent) gave the sub-title compound (177 mg).
MS: ESI (+ve and −ve): 371 [M+H]$^+$100% and 369 [M−H]$^-$100%

(ii) 5-Fluoro-2-methyl-3-[4-[(methylamino)carbonyl]phenoxy]-1H-indole-1-acetic acid A solution of the product from step a) (146 mg) and sodium hydroxide (0.4 ml, 1M) in THF (2 ml)—MeOH (1 ml) was stirred for 18 h. The solvent was removed in vacuo and the residue was washed with ether, acidifed (2M HCl) and extracted with ethyl acetate. The organic extracts were dried (MgSO$_4$), evaporated and crystallised from isohexane—acetone to give the title compound as a white solid (53 mg). M.p. 217-8° C.
MS: ESI (+ve and −ve): 357 [M+H]$^+$100% and 355 [M−H]$^-$100% $^1$H NMR DMSO-d6: δ 13.10 (1H, s), 8.29 (1H, d), 7.78 (2H, d), 7.52 (1H, dd), 6.99-6.91 (3H, m), 6.83 (1H, d), 5.04 (2H, s), 2.75 (3H, d), 2.19 (3H, s).

Example 11

3-[4-[(Ethylamino)carbonyl]phenoxy]-5-fluoro-2-methyl-1H-indole-1-acetic acid (iii) Methyl 3-[4-[(Ethylamino)carbonyl]phenoxy]-5-fluoro-2-methyl-1H-indole-1-acetate The sub-title compound was prepared by the method of Example 10, step a) using the product from Example 9 and ethylamine in THF.
MS: ESI (+ve): 384 [M+H]$^+$100%.

(iv) 3-[4-[(Ethylamino)carbonyl]phenoxy]-5-fluoro-2-methyl-1H-indole-1-acetic acid The title compound was prepared by the method of Example 10, step b) using the product from step a). M.p. 220-2° C.
MS: ESI (+ve): 370 [M+H]$^+$100%. $^1$H NMR DMSO-d6: δ 13.09 (1H, s), 8.33 (1H, d), 7.79 (2H, d), 7.52 (1H, dd), 6.99-6.91 (3H, m), 6.83 (1H, d), 5.04 (2H, s), 3.26 (2H, dq), 2.19 (3H, s), 1.10 (3H, t).

Example 12

5-Fluoro-2-methyl-3-[4-[[(1-methylethyl)amino]carbonyl]phenoxy]-1H-indole-1-acetic acid (i) Methyl 5-fluoro-2-methyl-3-[4-[[(1-methylethyl)amino]carbonyl]phenoxy]-1H-indole-1-acetic acid The sub-title compound was prepared by the method of Example 10, step a) using the product from Example 9 and isopropylamine.
MS: ESI (+ve): 399 [M+H]$^+$100%.

(ii) 5-Fluoro-2-methyl-3-[4-[[(1-methylethyl)amino]carbonyl]phenoxy]-1H-indole-1-acetic acid.

The title compound was prepared by the method of Example 10, step b) using the product from step a). M.p. 218-9° C.
MS: ESI (+ve): 385 [M+H]$^+$100%. $^1$H NMR DMSO-d6: δ 13.09 (1H, s), 8.07 (1H, d), 7.80 (2H, d), 7.52 (1H, dd), 6.99-6.91 (3H, m), 6.82 (1H, d), 5.04 (2H, s), 4.07 (1H, d heptet), 2.19 (3H, s), 1.10 (6H, d).

Example 13

3-(4-Carboxyphenoxy)-5-chloro-2-methyl-1H-indole-1-acetic acid (i) Methyl 4-[[(2Z)-2-[(4-fluorophenyl)hydrazono]propyl]oxy]-benzoate The sub-title compound was prepared from 4-chlorophenylhydrazine by the method of Example 9 step a).
MS: ESI (+ve): 317 [M+H]$^+$100%

(ii) Methyl 4-[(5-chloro-2-methyl-1H-indol-3-yl)oxy]-benzoate

The sub-title compound was prepared from the product of step a) by the method of Example 9 step b).
MS: ESI (–ve): 314 [M–H]$^-$100%

(iii) 1,1-Dimethylethyl 5-chloro-3-[4-(methoxycarbonyl)phenoxy]-2-methyl-1H-indole-1-acetate The sub-title compound was prepared from the product of step b) by the method of Example 9 step c).
MS: ESI (–ve): 428 [M–H]$^-$100%

(iv) 3-(4-Carboxyphenoxy)-5-chloro-2-methyl-1H-indole-1-acetic acid

A solution of the product from step c) (1.65 g) and sodium hydroxide (8.5 ml, 1M) in THF (15 ml) and methanol (10 ml) was stirred for 30 h. The solvent was removed in vacuo, the mixture was acidified with 2M HCl and extracted with ethyl acetate. The organic extracts were dried (MgSO$_4$), and evaporated to give a solid. Crystallisation from iso-hexane—acetone gave the title compound as an off-white solid (1.51 g). M.p 215-6° C.
$^1$H NMR DMSO-d6: δ 12.94 (1H, s), 7.91 (2H, d), 7.56 (1H, dd), 7.13 (1H, d), 7.21 (1H, s), 6.98 (2H, d), 5.06 (2H, s) 2.20 (3H, s). MS: ESI (+ve): 358 [M+H]$^+$100%

Example 14

5-Fluoro-3-[4-(methoxycarbonyl)phenoxy]-2-methyl-1H-indole-1-acetic acid

A solution of the product from Example 9 step c) (128 mg) in TFA (2 ml) and DCM (1 ml) was stirred for 2 h. The mixture was evaporated and purified by chromatography (silica, DCM-MeOH—AcOH as eluent) to give, after trituration with ether, the title compound (41 mg). M.p. 195-6° C.
MS: ESI (+ve): 358 [M+H]$^+$100%. $^1$H NMR DMSO-d6: δ 13.09 (1H, s), 7.93 (2H, d), 7.53 (1H, dd), 7.02-6.94 (3H, m), 6.85 (1H, d), 5.04 (2H, s), 3.81 (3H, s), 2.19 (3H, s).

Example 15

5-Chloro-3-[4-(methoxycarbonyl)phenoxy]-2-methyl-1H-indole-1-acetic acid

The title compound was prepared from the product from Example 13 step c) by the method of Example 14. M.p. 196-7° C.
MS: ESI (+ve): 374 [M+H]$^+$100%. $^1$H NMR DMSO-d6: δ 13.14 (1H, s), 7.94 (2H, d), 7.56 (1H, dd), 7.15-7.10 (2H, m), 7.00 (2H, d), 5.04 (2H, s), 3.81 (3H, s), 2.19 (3H, s).

Example 16

5-Chloro-2-methyl-3-[4-[(methylamino)carbonyl]phenoxy]-1H-indole-1-acetic acid (i) Methyl 5-chloro-2-methyl-3-[4-[(methylamino)carbonyl]phenoxy]-1H-indole-1-acetate The sub-title compound was prepared by the method of Example 10, step a) using the product from Example 13 and methylamine in THF.
MS: ESI (+ve): 384 [M+H]$^+$100%

(ii) 5-Chloro-2-methyl-3-[4-[(methylamino)carbonyl]phenoxy]-1H-indole-1-acetic acid The title compound was prepared by the method of Example 10, step b) using the product from step a). M.p. 225° C. (dec).

MS: ESI (+ve): 373 [M+H]$^+$100%. $^1$H NMR DMSO-d6: δ 8.30 (1H, d), 7.79 (2H, d), 7.55 (1H, dd), 7.12 (1H, d), 7.09 (1H, s), 6.94 (2H, d), 5.05 (2H, s), 2.76 (3H, s), 2.20 (3H, s).

Example 17

5-Chloro-3-[4-[(ethylamino)carbonyl]phenoxy]-2-methyl-1H-indole-1-acetic acid (i) Methyl 5-chloro-3-[4-[(ethylamino)carbonyl]phenoxy]-2-methyl-5H-indole-1-acetate The sub-title compound was prepared by the method of Example 10, step a) using the product from Example 13 and ethylamine in THF.

MS: ESI (+ve): 401 [M+H]$^+$100%

(ii) 5-Chloro-3-[4-[(ethylamino)carbonyl]phenoxy]-2-methyl-1H-indole-1-acetic acid The title compound was prepared by the method of Example 10, step b) using the product from step a). M.p. 220° C. (dec).

MS: ESI (+ve): 387 [M+H]$^+$100%. $^1$H NMR DMSO-d6: δ 7.81 (2H, d), 7.56 (1H, dd), 7.13 (1H,d d), 7.08 (1H, s), 6.94 (2H, d), 5.05 (2H, s), 3.26 (2H, dq), 2.20 (3H, s), 1.10 (3H, t).

Example 18

Sodium 5-Chloro-2-methyl-3-[4-[[(1-methylethyl)amino]carbonyl]phenoxy]-1H-indole-1-acetate (i) Methyl 5-chloro-2-methyl-3-[4-[[(1-methylethyl)amino]carbonyl]phenoxy]-1H-indole-1-acetate The sub-title compound was prepared by the method of Example 10, step a) using the product from Example 13 and isopropylamine.

MS: ESI (+ve): 415 [M+H]$^+$100%

(ii) Sodium 5-Chloro-2-methyl-3-[4-[[(1-methylethyl)amino]carbonyl]phenoxy]-1H-indole-1-acetate A solution of the product from step a) (102 mg) and sodium hydroxide (0.25 ml, 1M) in THF (2 ml)—MeOH (3 ml) was stirred for 2 days. The solvent was removed in vacuo and the residue was washed with ether, and water, collected, and dried to give the title compound as a white solid (71 mg). M.p.<275° C.

MS: ESI (+ve): 401 [M+H]$^+$100%. $^1$H NMR DMSO-d6: δ 8.09 (1H, d), 7.79 (2H, d), 7.35 (1H, dd), 7.03-7.00 (2H, m), 6.93 (2H, d), 4.41 (2H, s), 4.07 (1H, d heptet), 2.17 (3H, s), 1.14 (6H, d).

Example 19

3-[4-[[(2-Aminoethyl)amino]carbonyl]phenoxy]-5-fluoro-2-methyl-1H-indole-1-acetic acid (i) Methyl 3-[4-[[[2-[[(1,1-dimethylethoxy)hydroxymethyl]amino]ethyl]amino]carbonyl]phenoxy]-5-fluoro-2-methyl-1H-indole-1-acetate The sub-title compound was prepared by the method of Example 10, step a) using the product from Example 13 and 1,1-dimethylethyl 3-aminopropylcarbamate.

MS: ESI (−ve): 588 [M+AcO]$^-$100% $^1$H NMR CDCl$_3$: δ 7.79 (2H, d), 7.24 (1H, s), 7.14 (2H, s), 7.10 (1H, s), 6.97 (2H, d), 4.89 (1H, s), 4.80 (2H, s), 3.77 (3H, s), 3.49 (2H, q), 3.24 (2H, q), 2.26 (3H, s), 1.70 (1H, tt), 1.45 (9H, s).

(ii) 3-[4-[[[2-[[(1,1-Dimethylethoxy)hydroxymethyl]amino]ethyl]amino]carbonyl]phenoxy]-5-fluoro-2-methyl-1H-indole-1-acetic acid A solution of the product from step a) 9121 mg) in TFA (1 ml) and DCM (1 ml) was stirred for 2 h. The solvent was removed in vacuo, aq sodium bicarbonate was added and the mixture was extracted with ethyl acetate (3 times) and DCM (3 times). The organic extracts were dried (MgSO$_4$ and, evaporated to give the sub-title compound (95 mg).

MS: ESI (+ve): 430 [M+H]$^+$100%.

(iii) 3-[4-[[(2-Aminoethyl)amino]carbonyl]phenoxy]-5-fluoro-2-methyl-1H-indole-1-acetic acid The title compound was prepared by the method of Example 10, step b) using the product from step b).

MS: ESI (+ve): 416 [M+H]$^+$100%. $^1$H NMR DMSO-d6: δ 8.44 (1H, t), 7.81 (2H, d), 7.56 (1H, dd), 7.13 (1H,dd), 7.08 (1H, s), 6.94 (2H, d), 5.05 (2H, s), 3.26 (2H, dq), 2.20 (3H, s), 1.10 (3H, t).

Example 20

2,5-Dimethyl-3-[4-(methylsulfonyl)phenoxy]-1H-indole-1-acetic acid (i) 1-[4-(Methylsulfonyl)phenoxy]-2-propanone 3-Chloroperoxybenzoic acid (5.7 g) was added portionwise to a solution of the product from example 2 step (i) (1.8 g) in DCM (100 ml) and the reaction stirred for 2 h. The mixture was washed with 10% aqueous sodium metabisulphite, saturated sodium bicarbonate, water and brine, dried (MgSO$_4$), filtered and evaporated in vacuo. The residue was purified by chromatography on silica eluting with 50% ethylacetate/iso-hexane. Yield 600 mg.

$^1$H NMR DMSO-d6 δ 7.90 (d, 2H), 7.29 (d, 2H), 5.87 (s, 2H), 2.09 (s, 3H) MS: APCI (+ve): 229 (M+1).

(ii) 1-[4-(Methylsulfonyl)phenoxy]-2-propanone, (4-methylphenyl)hydrazone

The product from step (i) (1 g) and 4-methylphenylhydrazine (540 mg) were dissolved in ethanol (50 ml) and stirred for 1 h. The mixture was evaporated and azeotroped with toluene to give a brown solid. Yield 1.2 g.

MS: APCI (+ve): 333 (M+1).

(iii) 2,5-Dimethyl-3-[4-(methylsulfonyl)phenoxy]-1H-indole

Phosphorous trichloride (200 g) was added to a solution of the product from step (ii) (1.1 g) in THF (50 ml) and the reaction stirred for 20 h. The mixture was diluted with EtOAc (100 ml), washed with water, saturated sodium bicarbonate and brine, dried (MgSO$_4$), filtered and evaporated in vacuo. The residue was purified by chromatography on silica eluting with 50% ethylacetate/iso-hexane. Yield 530 mg.

$^1$H NMR DMSO-d6 δ 10.90 (s, 1H), 7.85 (d, 2H), 7.22 (d, 1H), 7.09 (d, 2H), 6.88 (d, 1H), 6.87 (s, 1H), 3.17 (s, 3H), 2.28 (s, 3H), 2.22 (s, 3H) MS: APCI (+ve): 316 (M+1).

(iv) 2,5-Dimethyl-3-[4-(methylsulfonyl)phenoxy]-1H-indole-1-acetic acid

Sodium t-butoxide (220 mg) was added to a solution of the product from step (iii) (600 mg) in THF (20 ml) and stirred for 10 min. Ethyl bromoacetate (250 μl) was added and the reaction stirred for a further 1 h. The mixture was then diluted with water (10 ml), 1M aqueous sodium hydroxide (5 ml) added and stirred for 3 h. The mixture was extracted with EtOAc, washed with brine, dried (MgSO$_4$), filtered and evaporated. The residue was purified using reverse phase preparative chromatography (eluent MeCN/NH$_3$(aq)) to give the title compound. Yield 450 mg.

$^1$H NMR DMSO-d6 δ 7.85 (d, 2H), 7.27 (d, 1H), 7.10 (d, 2H), 6.90 (d, 1H), 6.89 (s, 1H), 4.62 (s, 2H), 3.17 (s, 3H), 2.29 (s, 3H), 2.15 (s, 3H) MS: APCI (−ve): 372 (M−1).

Example 21

2-Methyl-3-[4-(methylsulfonyl)phenoxy]-5-(trifluoromethyl)-1H-indole-1-acetic acid

(i) 1-[4-(Methylsulfonyl)phenoxy]-2-propanone, [4-(trifluoromethyl) phenyl]hydrazone The sub-title compound was prepared by the method of example 20 step (ii), using the product from example 20 step (i) (600 mg) and 4-(trifluoromethyl)phenylhydrazine (460 mg). Yield 1.0 g.

MS: APCI (+ve): 387 (M+1).

(ii) 2-Methyl-3-[4-(methylsulfonyl)phenoxy]-5-(trifluoromethyl)-1H-indole

The sub-title compound was prepared by the method of example 20 step (iii), using the product from step (i) (800 mg). Yield 520 mg.

$^1$H NMR DMSO-d6 δ 11.61 (s, 1H), 7.87 (d, 2H), 7.55 (d, 1H), 7.45 (s, 1H), 7.13 (d, 2H), 6.95 (d, 1H), 3.18 (s, 3H), 2.29 (s, 3H) MS: APCI (+ve): 370 (M+1).

(iii) 2-Methyl-3-[4-(methylsulfonyl)phenoxy]-5-(trifluoromethyl)-1H-indole-1-acetic acid The title compound was prepared by the method of example 20 step (iv), using the product from step (ii) (500 mg). Yield 320 mg.

$^1$H NMR DMSO-d6 δ 7.87 (d, 2H), 7.61 (d, 1H), 7.44 (s, 1H), 7.36 (d, 1H), 7.12 (d, 2H), 4.61 (s, 21H), 3.18 (s, 3H), 1.75 (s, 3H) MS: APCI (−ve): 426 (M−1)

Example 22

5-Chloro-α,2-dimethyl-3-[4-(methylsulfonyl)phenoxy]-1H-indole-1-acetic acid

(i) 1-[4-(Methylsulfonyl)phenoxy]-2-propanone, (4-chlorophenyl)hydrazone

The sub-title compound was prepared by the method of example 20 step (ii), using the product from example 20 step (i) (700 mg) and 4-chlorophenylhydrazine (430 mg). Yield 900 mg.

$^1$H NMR DMSO-d6 δ 9.26 (s, 1H), 7.85 (d, 2H), 7.10 (d, 2H), 7.23 (d, 2H), 7.21 (d, 2H), 4.76 (s, 2H), 3.32 (s, 3H), 1.96 (s, 3H) MS: APCI (+ve): 353 (M+1).

(ii) 5-Chloro-2-methyl-3-[4-(methylsulfonyl)phenoxy]-1H-indole

The sub-title compound was prepared by the method of example 20 step (iii), using the product from step (i) (800 mg). Yield 450 mg.

$^1$H NMR DMSO-d6 δ 11.32 (s, 1H), 7.87 (d, 2H), 7.36 (d, 1H), 7.09 (m, 4H), 3.18 (s, 3H), 2.25 (s, 3H) MS: APCI (+ve): 370 (M+1).

(iii) 5-Chloro-2-methyl-3-[4-(methylsulfonyl)phenoxy]-1H-indole-1-acetic acid The title compound was prepared by the method of example 20 step (iv), using the product from step (ii) (350 mg). Yield 300 mg.

$^1$H NMR DMSO-d6 δ 7.86 (d, 2H), 7.43 (d, 1H), 7.09 (m, 4H), 4.61 (s, 2H), 3.18 (s, 3H), 2.17 (s, 3H) MS: APCI (−ve): 393 (M−1)

Example 23

5-Cyano-2-methyl-3-[4-(methylsulfonyl)phenoxy]-1H-indole-1-acetic acid

(i) 4-[2-[1-Methyl-2-[4-(methylsulfonyl)phenoxy] ethylidene]hydrazino]-benzonitrile The sub-title compound was prepared by the method of example 20 step (ii), using the product from example 20 step (i) (700 mg) and 4-cyanophenylhydrazine (400 mg). Yield 900 mg.

MS: APCI (+ve): 344 (M+1).

(ii) 2-Methyl-3-[4-(methylsulfonyl)phenoxy]-1H-indole-5-carbonitrile

The sub-title compound was prepared by the method of example 20 step (iii), using the product from step (i) (450 mg). Yield 320 mg.

$^1$H NMR DMSO-d6 δ 7.87 (d, 2H), 7.64 (s, 1H), 7.52 (d, 1H), 7.44 (d, 1H), 7.12 (d, 2H), 3.18 (s, 3H), 2.28 (s, 3H) MS: APCI (+ve): 327 (M+1).

(iii) 5-Cyano-2-methyl-3-[4-(methylsulfonyl)phenoxy]-1H-indole-1-acetic acid The title compound was prepared by the method of example 20 step (iv), using the product from step (ii) (270 mg). Yield 150 mg.

$^1$H NMR DMSO-d6 δ 7.88 (d, 2H), 7.70 (d, 1H), 7.68 (s, 1H), 7.48 (d, 1H), 7.11 (d, 2H), 4.97 (s, 2H), 3.18 (s, 3H), 2.22 (s, 3H) MS: APCI (−ve): 383 (M−1)

Example 24

3-(4-Chlorophenoxy)-4-[(ethylsulfonyl)amino]-2-methyl-1H-indole-1-acetic acid

(i) 1-(4-Chlorophenoxy)-2-propanone, (3-nitrophenyl)hydrazone

3-Nitrophenylhydrazine hydrochloride (25.0 g) was stirred in a mixture of EtOAc and aqueous sodium bicarbonate for 30 min. The layers were separated, the aqueous extracted with EtOAc and the combined extracts (1000 ml) washed with brine, dried (MgSO$_4$) and filtered. Ethanol (200 ml) was added to the filtrate, followed by 1-(4-chlorophenoxy)-propan-2-one (23.9 g) and stirred for 5 h. The mixture was evaporated and the residue treated with ether/isohexane (1:1) to give a light brown solid. Yield 30.0 g.

MS: APCI (+ve): 320 (M+1).

(ii) 3-(4-Chlorophenoxy)-2-methyl-4-nitro-1H-indole

The product from step (i) (29.0 g) was dissolved in THF (1000 ml), sodium bicarbonate (75.6 g) added, followed by phosphorous trichloride (37.1 ml) and heated at 70° C. for 20 h. The reaction was cooled to RT, diluted with EtOAc (1000 ml), washed with water and brine, dried (MgSO$_4$), filtered and evaporated. The residue was purified by chromatography on silica eluting with 20% ethylacetate/iso-hexane. Yield 6 g.

$^1$H NMR DMSO-d6 δ 7.83 (d, 1H), 7.77 (d, 1H), 7.29 (d, 2H), 7.23 (t, 1H), 6.80 (d, 2H), 2.28 (s, 3H) MS: APCI (+ve): 303 (M+1).

(iii) 3-(4-Chlorophenoxy)-2-methyl-4-nitro-1H-indole-1-acetic acid, ethyl ester The product from step (ii) (6.0 g) was dissolved in THF (100 ml), sodium t-butoxide (2.1 g) added, stirred for 10 min, ethyl bromoacetate (2.45 ml) added and stirred for a further 20 min. The reaction was quenched with 1M hydrochloric acid, extracted with EtOAc, washed with brine, dried (MgSO$_4$), filtered and evaporated. The residue was purified by chromatography on silica eluting with 20% ethylacetate/iso-hexane. Yield 6 g.

$^1$H NMR DMSO-d6 δ 8.02 (d, 1H), 7.86 (d, 1H), 7.32 (d, 2H), 7.30 (t, 1H), 6.80 (d, 2H), 5.33 (s, 2H), 4.18 (q, 2H), 2.23 (s, 3H), 1.22 (t, 3H) MS: APCI (+ve): 389 (M+1).

(iv) 4-Amino-3-(4-chlorophenoxy)-2-methyl-1H-indole-1-acetic acid, ethyl ester The product from step (iii) (1.0 g) was dissolved in EtOAc (20 ml), triethylamine (1.1 ml) added, followed by 5% Pt/C (50 mg) and hydrogenated at 1 atm and RT for 6 h. The catalyst was filtered off and the filtrate evaporated to give a light brown solid. Yield 800 mg.

$^1$HNMR DMSO-d6 δ 7.36 (d, 2H), 6.93 (d, 2H), 6.80 (t, 1H), 6.62 (d, 1H), 6.15 (d, 1H), 4.97 (s, 2H), 4.68 (s, 2H), 4.15 (q, 2H), 2.07 (s, 3H), 1.20 (t, 3H) MS: APCI (+ve): 359 (M+1).

(v) 3-(4-Chlorophenoxy)-4-[(ethylsulfonyl)amino]-2-methyl-1H-indole-1-acetic acid The product from step (iv) (250 mg) was dissolved in CH$_3$CN (10 ml). Triethylamine (300 μl) added, followed by ethanesulphonyl chloride (170 μl) and the mixture stirred for 20 h. The reaction was then diluted with MeOH (5 ml), 1M sodium hydroxide (2.1 ml) added and stirred for 5 h. The mixture was diluted with water, acidified with 2M hydrochloric acid, extracted with EtOAc, dried (MgSO$_4$) and evaporated. The residue was purified using reverse phase preparative chromatography (eluent MeCN/NH$_3$(aq)) to give the title compound. Yield 190 mg.

$^1$H NMR DMSO-d6 δ 7.33 (d, 2H), 7.28 (d, 1H), 7.03 (t, 1H), 6.88 (d, 2H), 6.88 (d, 1H), 4.80 (s, 2H), 2.88 (q, 2H), 2.11 (s, 3H), 1.04 (t, 3H) MS: APCI (−ve): 421 (M−1)

Example 25

3-(4-Chlorophenoxy)-4-[[(dimethylamino)sulfonyl]amino]-2-methyl-1H-indole-1-acetic acid The title compound was prepared by the method of example 25 step (v), using the product from example 25 step (iv) (250 mg) and dimethylsulfamoyl chloride and heating at 60° C. Yield 80 mg.

$^1$H NMR DMSO-d6 δ 7.33 (d, 2H), 7.24 (d, 1H), 7.02 (t, 1H), 6.95 (d, 1H), 6.89 (d, 2H), 4.85 (s, 2H), 2.55 (s, 6H), 2.11 (s, 3H) MS: APCI (−ve): 436 (M−1)

Example 26

3-(4-Chlorophenoxy)-2-methyl-4-pyrazinyl-1H-indole-1-acetic acid

(i) 3-(4-Chlorophenoxy)-4-iodo-2-methyl-1H-indole-1-acetic acid, ethyl ester The product from example 25 step (iv) (1.5 g) was treated with 10% aqueous sulphuric acid (50 ml) and cooled to 0° C. A solution of sodium nitrite (350 mg) in water (3 ml) was added dropwise and the reaction stirred for 15 min. A solution of potassium iodide (2.1 g) in water (5 ml) was added all at once and the reaction allowed to attain RT over 1 h. The mixture was extracted with EtOAc, washed with aqueous sodium thiosulphate, water and brine, dried (MgSO4), filtered and evaporated. The residue was purified by chromatography on silica eluting with 20% ethylacetate/iso-hexane. Yield 280 mg.

$^1$HNMR CDCl$_3$ δ 7.52 (d, 1H), 7.21 (d, 1H), 7.21 (d, 2H), 6.89 (t, 1H), 6.82 (d, 2H), 4.79 (s, 2H), 4.22 (q 2H), 2.21 (s, 3H), 1.26 (t, 3H) MS: APCI (+ve): 470 (+1).

(ii) 3-(4-Chlorophenoxy)-2-methyl-4-pyrazinyl-1H-indole-1-acetic acid

The product from step (i) (250 mg), 2-(tributylstannyl)-pyrazine (260 mg), Pd (dba)$_2$ (30 mg) and triphenyl-arsine (210 mg) were dissolved in toluene (4 ml) and heated at 90° C. for 20 h. The reaction was cooled to RT, methanol (10 ml) added, followed by 1M aqueous sodium hydroxide (2 ml) and stirred for 20 h. The mixture was diluted with water, extracted with EtOAc, washed with brine, dried (MgSO$_4$), filtered and evaporated. The residue was purified using reverse phase preparative chromatography (eluent MeCN/NH$_3$(aq)) to give the title compound. Yield 30 mg.

$^1$H NMR DMSO-d6 δ 8.69 (s, 1H), 8.44 (m, 1H), 8.41 (d, 1H), 7.64 (d, 1H), 7.26 (t, 1H), 7.20 (d, 1H), 7.08 (d, 2H), 6.42 (d, 2H), 5.07 (s, 2H), 2.20 (s, 3H) MS: APCI (−ve): 392 (M−1)

Example 27

3-(4-Chlorophenoxy)-2-methyl-4-[[(1-methylethyl)sulfonyl]amino]-1H-indole-1-acetic acid The product from example 25 step (iv) (250 mg) was dissolved in pyridine (2 ml), treated with 2-propanesulfonyl chloride (200 μl) and heated at 50° C. for 5 h. The reaction was acidified with 2M hydrochloric acid, extracted with EtOAc, washed with water and brine, dried (MgSO$_4$), filtered and evaporated. The residue was dissolved in methanol (10 ml), treated with 1M sodium hydroxide (2 ml) and stirred for 5 h. The mixture was diluted with water, acidified with 2M hydrochloic acid, extracted with EtOAc, washed with brine, dried (MgSO$_4$), filtered and evaporated. The residue was purified using reverse phase preparative chromatography (eluent MeCN/NH$_3$(aq)) to give the title compound. Yield 30 mg.

$^1$H NMR DMSO-d6 δ 7.34 (d, 2H), 7.28 (d, 1H), 7.04 (t, 1H), 6.92 (d, 1H), 6.88 (d, 2H), 4.88 (s, 2H), 3.13 (m, 1H), 2.11 (s, 3H), 1.11 (d, 6H) MS: APCI (−ve): 435 (M−1)

Example 28

3-[4-[(Dimethylamino)sulfonyl]phenoxy]-5-fluoro-2-methyl-1H-indole-1-acetic acid (i) N,N-Dimethyl-4-(2-oxopropoxy)-benzenesulfonamide The sub-title compound was prepared by the method of example 2 step (i) using 4-hydroxy-N,N-dimethylbenzenesulfonamide (4.3 g). Yield 4.2 g.

$^1$H NMR DMSO-d6 δ 7.66 (d, 2H), 7.12 (d, 2H), 3.32 (s, 2H), 2.57 (s, 6H), 2.17 (s, 3H) MS: APCI (+ve): 258 (+1).

(ii) 4-[[(2-[(4-Fluorophenyl)hydrazono]propyl]oxy]-N,N-dimethyl-benzenesulfonamide The sub-title compound was prepared by the method of example 20 step (ii), using the product from step (i) (1.6 g) and 4-fluorophenylhydrazine (800 mg). Yield 2.2 g.

MS: APCI (+ve): 366 (M+1).

(iii) 4-[(5-Fluoro-2-methyl-1H-indol-3-yl)oxy]-N,N-dimethyl benzenesulfonamide

The sub-title compound was prepared by the method of example 20 step (iii), using the product from step (ii) (2.0 g). Yield 500 mg.

$^1$H NMR DMSO-d6 δ 11.18 (s, 1H), 7.70 (d, 2H), 7.33 (m, 1H), 7.11 (d, 2H), 6.90 (m, 1H), 6.83 (d, 1H), 2.59 (s, 6H), 2.25 (s, 3H) MS: APCI (+ve): 349 (M+1).

(iv) 3-[4-[(Dimethylamino)sulfonyl]phenoxy]-5-fluoro-2-methyl-1H-indole-1-acetic acid The title compound was prepared by the method of example 20 step (iv), using the product from step (iii) (270 mg). Yield 80 mg.

$^1$H NMR DMSO-d6 δ 7.70 (d, 2H), 7.50 (m, 1H), 7.11 (d, 2H), 6.95 (m, 1H), 6.88 (d, 1H), 4.94 (s, 2H), 2.59 (s, 6H), 2.19 (s, 3H) MS: APCI (−ve): 405 (M−1)

Example 29

3-[4-(Ethylsulfonyl)phenoxy]-5-fluoro-2-methyl-1H-indole-1-acetic acid (i) 1-[4-(Ethylthio)phenoxy]-2-propanone The sub-title compound was prepared by the method of example 2 step (i) using 4-(ethylthio)phenol (20.0 g). Yield 21.2 g.

$^1$H NMR DMSO-d6 δ 7.29 (d, 2H), 6.87 (d, 2H), 4.80 (s, 2H), 2.85 (q, 2H), 2.15 (s, 3H), 1.16 (t, 3H) MS: APCI (+ve): 211 (M+1).

(ii) 1-[4-(Ethylthio)phenoxy]-2-propanone, (4-fluorophenyl)hydrazone

The sub-title compound was prepared by the method of example 20 step (ii), using the product from step (i) (1.6 g) and 4-fluorophenylhydrazine (1.0 g). Yield 2.4 g.

MS: APCI (+ve): 319 (M+1). $^1$H NMR DMSO-d6 δ 7.30 (d, 2H), 7.09 (m, 2H), 7.03 (d, 2H), 6.98 (d, 2H), 4.61 (s, 2H), 2.85 (q, 2H), 1.94 (s, 3H), 1.16 (t, 3H) MS: APCI (+ve): 319 (M+1).

(iii) 3-[4-(Ethylthio)phenoxy]-5-fluoro-2-methyl-1H-indole

The sub-title compound was prepared by the method of example 20 step (iii), using the product from step (ii) (890 mg). Yield 800 mg.

MS: APCI (+ve): 302 (M+1).

(iv) 3-[4-(Ethylsulfonyl)phenoxy]-5-fluoro-2-methyl-1H-indole

3-Chloroperoxybenzoic acid (1.14 g) was added portionwise to a solution of the product from step (iii) (800 mg) in DCM (20 ml) and the reaction stirred for 1 h. The mixture was evaporated and purified by chromatography on silica eluting with 25% ethylacetate/iso-hexane. Yield 200 mg.

$^1$H NMR DMSO δ 11.19 (s, 1H), 7.82 (d, 2H), 7.34 (m, 1H), 7.11 (d, 2H), 6.91 (m, 1H), 6.83 (d, 1H), 3.24 (q, 2H), 2.25 (s, 3H), 1.10 (t, 3H) MS: APCI (+ve): 334 (M+1).

(v) 3-[4-(Ethylsulfonyl)phenoxy]-5-fluoro-2-methyl-1H-indole-1-acetic acid

The title compound was prepared by the method of example 20 step (iv), using the product from step (iv) (160 mg). Yield 130 mg.

$^1$H NMR DMSO-d6 δ 7.81 (d, 2R), 7.43 (m, 1H), 7.12 (d, 2H), 6.91 (m, 1H), 6.85 (d, 1H), 4.71 (s, 2H), 3.23 (q, 2H), 2.18 (s, 3H), 1.10 (t, 3H) MS: APCI (−ve): 390 (M−1)

Example 30

3-[4-(Ethylsulfonyl)phenoxy]-2-methyl-5-(trifluoromethyl)-1H-indole-1-acetic acid

(i) 1-[4-(ethylthio)phenoxy]-2-propanone, [4-(trifluoromethyl) phenyl]hydrazone

The sub-title compound was prepared by the method of example 20 step (ii), using the product from example 30 step (i) (2.1 g) and 4-(trifluoromethyl)phenylhydrazine (1.7 g). Yield 3.5 g.

MS: APCI (+ve): 369 (M+1).

(ii) 3-[4-(Ethylthio)phenoxy]-2-methyl-5-(trifluoromethyl)-1H-indole

The sub-title compound was prepared by the method of example 20 step (iii), using the product from step (i) (3.2 g). Yield 1.5 g.

MS: APCI (+ve): 352 (M+1).

(iii) 3-[4-(Ethylsulfonyl)phenoxy]-2-methyl-5-(trifluoromethyl)-1H-indole

A solution of oxone (1.0 g) in water (30 ml) was added to a solution of the product from step (ii) (1.4 g) in acetonitrile (100 ml) and stirred for 2 h. Further oxone (500 mg) was added and the reaction stirred for a further 3 h. The mixture was evaporated to ~50 ml, extracted with EtOAc, washed with aqueous sodium metabisulphite and brine, dried ($MgSO_4$), filtered and evaporated. The residue was purified by chromatography on silica eluting with 30% etlhylacetate/iso-hexane.

Yield 1.2 g.

$^1$H NMR DMSO-d6 δ 11.61 (s, 1H), 7.83 (d, 2H), 7.55 (d, 1H), 7.44 (s, 1H), 7.38 (d, 1H), 7.14 (d, 2H), 3.24 (q, 2H), 2.29 (s, 3H), 1.10 (t, 3H) MS: APCI (+ve): 384 (M+1).

(iv) 3-[4-(Ethylsulfonyl)phenoxy]-2-methyl-5-(trifluoromethyl)-1H-indole-1-acetic acid The title compound was prepared by the method of example 20 step (iv), using the product from step (iii) (1.1 g). Yield 380 mg.

$^1$HNMR DMSO δ 7.83 (d, 2H), 7.66 (d, 1H), 7.45 (s, 1H), 7.39 (d, 1H), 7.14 (d, 2H), 4.83 (s, 2H), 3.24 (q, 2H), 2.22 (s, 3H), 1.09 (t, 3H) MS: APCI (−ve): 440 (M−1)

Example 31

3-(4Cyanophenoxy)-2-methyl-5-(trifluoromethyl)-1H-indole-1-acetic acid

(i) 4-(2-Oxopropoxy)benzonitrile

The sub-title compound was prepared by the method of example 2 step (i) using 4-hydroxybenzonitrile (15.5 g). Yield 22.5 g.

$^1$H NMR DMSO-d6 δ 7.75 (d, 2H), 7.08 (d, 2H), 4.98 (s, 2H), 2.15 (s, 3H) MS: APCI (+ve): 174 (M+1).

(ii) 4-[[2-[[4-(Trifluoromethyl)phenyl]hydrazono]propyl]oxy]benzonitrile

The sub-title compound was prepared by the method of example 20 step (ii), using the product from step (i) (3.8 g) and 4-(trifluoromethyl)phenylhydrazine (3.7 g). Yield 2.8 g.

$^1$H NMR DMSO-d6 δ 9.61 (s, 1H), 7.78 (d, 2H), 7.51 (d, 2H), 7.23 (d, 2H), 7.19 (d, 2H), 4.78 (s, 2H), 2.00 (s, 3H) MS: APCI (+ve): 334 (M+1).

(iii) 4-[[2-Methyl-5-(trifluoromethyl)-1H-indol-3-yl]oxy]-benzonitrile

The sub-title compound was prepared by the method of example 20 step (iii), using the product from step (ii) (2.6 g). Yield 1.7 g.

$^1$H NMR DMSO-d6 δ 11.61 (s, 1H), 7.80 (d, 2H), 7.55 (d, 1H), 7.42 (s, 1H), 7.38 (d, 1H), 7.08 (d, 2H), 2.29 (s, 3H) MS: APCI (+ve): 317 (M+1).

(iv) 3-(4-Cyanophenoxy)-2-methyl-5-(trifluoromethyl)-1H-indole-1-acetic acid

The title compound was prepared by the method of example 20 step (iv), using the product from step (iii) (1.4 g). Yield 720 mg.

$^1$H NMR DMSO-d6 δ 7.80 (d, 2H), 7.62 (d, 1H), 7.42 (s, 1H), 7.36 (d, 1H), 7.07 (d, 2H), 4.66 (s, 2H), 2.20 (s, 3H) MS: APCI (−ve): 373 (M−1).

Example 32

3-(4-Cyanophenoxy)-5-fluoro-2-methyl-1H-indole-1-acetic acid

(i) 4-[[(2-[(4-Fluorophenyl)hydrazono]propyl]oxy]benzonitrile

The sub-title compound was prepared by the method of example 20 step (ii), using the product from example 32 step (i) (3.8 g) and 4-fluorophenylhydrazine (2.7 g). Yield 2.9 g.

$^1$H NMR DMSO-d6 δ 9.10 (s, 1H), 7.78 (d, 2H), 7.18 (d, 2H), 7.05 (m, 4H), 4.73 (s, 2H), 1.94 (s, 3H) MS: APCI (+ve): 284 (M+1).

(ii) 4-[(5-Fluoro-2-methyl-1H-indol-3-yl)oxy]benzonitrile

The sub-title compound was prepared by the method of example 20 step (iii), using the product from step (i) (2.8 g). Yield 1.4 g.

$^1$H NMR DMSO-d6 δ 11.20 (s, 1H), 7.78 (d, 2H), 7.34 (m, 1H), 7.05 (d, 2H), 6.91 (m, 1H), 6.81 (d, 1H), 2.24 (s, 3H) MS: APCI (+ve): 267 (M+1).

(iii) 3-(4-Cyanophenoxy)-5-fluoro-2-methyl-1H-indole-1-acetic acid

The title compound was prepared by the method of example 20 step (iv), using the product from step (ii) (1.2 g). Yield 430 mg.

$^1$H NMR DMSO-d6 δ 7.78 (d, 2H), 7.38 (m, 1H), 7.05 (d, 2H), 6.89 (m, 1H), 6.81 (d, 1H), 4.52 (s, 2H), 2.15 (s, 3H) MS: APCI (−ve): 323 (M−1).

Pharmacological Data

Ligand Binding Assay

[³H]PGD$_2$ was purchased from Perkin Elmer Life Sciences with a specific activity of 100-210 Ci/mmol. All other chemicals were of analytical grade.

HEK cells expressing rhCRTh2/Gα16 were routinely maintained in DMEM containing 10% Foetal Bovine Serum (HyClone), 1 mg/ml geneticin, 2 mM L-glutamine and 1% non-essential amino acids. For the preparation of membranes, the adherent transfected HEK cells were grown to confluence in two layer tissue culture factories (Fisher, catalogue number TKT-170-070E). Maximal levels of receptor expression were induced by addition of 500 mM sodium butyrate for the last 18 hours of culture. The adherent cells were washed once with phosphate buffered saline (PBS, 50 ml per cell factory) and detached by the addition of 50 ml per cell factory of ice-cold membrane homogenisation buffer [20 mM HEPES (pH 7.4), 0.1 mM dithiothreitol, 1 mM EDTA, 0.1 mM phenyl methyl sulphonyl fluoride and 100 μg/ml bacitracin]. Cells were pelleted by centrifugation at 220×g for 10 minutes at 4° C., re-suspended in half the original volume of fresh membrane homogenisation buffer and disrupted using a Polytron homogeniser for 2×20 second bursts keeping the tube in ice at all times. Unbroken cells were removed by centrifugation at 220×g for 10 minutes at 4° C. and the membrane fraction pelleted by centrifugation at 90000×g for 30 minutes at 4° C. The final pellet was re-suspended in 4 ml of membrane homogenisation buffer per cell factory used and the protein content determined.

Membranes were stored at −80° C. in suitable aliquots.

All assays were performed in Corning clear bottomed, white 96-well NBS plates (Fisher). Prior to assay, the HEK cells membranes containing CRTh2 were coated onto SPA PVT WGA beads (Amersham). For coating membranes were incubated with beads at typically 25 μg membrane protein per mg beads at 4° C. with constant agitation overnight. (The optimum coating concentrations were determined for each batch of membranes) The beads were pelleted by centrifugation (800×g for 7 minutes at 4° C.), washed once with assay buffer (50 mM HEPES pH 7.4 containing 5 mM magnesium chloride) and finally re-suspended in assay buffer at a bead concentration of 10 mg/ml.

Each assay contained 20 μl of 6.25 nM [³H]PGD$_2$, 20 μl membrane saturated SPA beads both in assay buffer and 10 μl of compound solution or 13,14-dihydro-15-keto prostaglandin D$_2$ (DK-PGD$_2$, for determination of non-specific binding, Cayman chemical company). Compounds and DK-PGD$_2$ were dissolved in DMSO and diluted in the same solvent to 100× the required final concentration. Assay buffer was added to give a final concentration of 10% DMSO (compounds were now at 10× the required final concentration) and this was the solution added to the assay plate. The assay plate was incubated at room temperature for 2 hours and counted on a Wallac Microbeta liquid scintillation counter (1 minute per well).

Compounds of formula (I) have an IC$_{50}$ value of less than (<) 10 μM.

Specifically example 9 has a pIC50=6.75, example 5 has a pIC50=7.05 and example 6 has a pIC50 7.95.

The invention claimed is:

1. A compound of formula (I) or a pharmaceutically acceptable salt thereof:

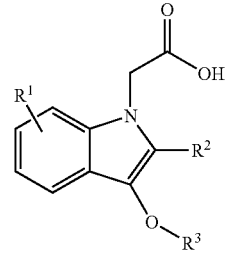

(I)

in which
R$^1$ is one or more substituents selected from hydrogen, halogen, CN, nitro, SO$_2$R$^4$, OH, OR$^4$, S(O)xR$^4$, SO$_2$NR$^5$R$^6$, CONR$^5$R$^6$, NR$^5$R$^6$, NR$^9$SO$_2$R$^4$, NR$^9$SO$_2$NR$^5$R$^6$, NR$^9$CO$_2$R$^4$, NR$^9$COR$^4$, aryl, heteroaryl, C$_2$-C$_6$ alkenyl, C$_2$-C$_6$ alkynyl or C$_1$-C$_6$ alkyl, the latter five groups being optionally substituted by one or more substituents independently selected from halogen, CN, NR$^9$SO$_2$R$^4$, NR$^9$CO$_2$R$^4$, NR$^9$COR$^4$, OR$^8$ and NR$^5$R$^6$, S(O)$_x$R$^7$ where x is 0, 1 or 2;

R$^2$ is hydrogen, halogen, CN, SO$_2$R$^4$ or CONR$^5$R$^6$, CH$_2$OH, CH$_2$OR$^4$ or C$_{1-7}$alkyl, the latter group being optionally substituted by one or more substituents independently selected from halogen atoms, OR$^8$ and NR$^5$R$^6$, S(O)$_x$R$^7$ where x is 0, 1 or 2;

R$^3$ is aryl or heteroaryl each of which is optionally substituted by one or more substituents independently selected from hydrogen, halogen, CN, nitro, OH, SO$_2$R$^4$, OR$^4$, SR$^4$, SOR$^4$, SO$_2$NR$^5$R$^6$, CONR$^5$R$^6$, NR$^5$R$^6$, NHSO$_2$R$^4$, NHCO$_2$R$^4$, NHCOR$^4$, NR$^7$SO$_2$R$^4$, NR$^7$CO$_2$R$^4$, NR$^7$COR$^4$, NHC$_{1-6}$alkylNR$^5$R$^6$, C$_2$-C$_6$ alkenyl, C$_2$-C$_6$ alkynyl, C$_{1-6}$ alkyl, the latter three groups being optionally substituted by one or more substituents independently selected from halogen atoms, CN, OR$^8$ and NR$^5$R$^6$, S(O)$_x$R$^7$ where x=0, 1 or 2;

R$^4$ represents aryl, heteroaryl, or C$_{1-6}$alkyl all of which may be optionally substituted by one or more substituents independently selected from halogen atoms, aryl, heteroaryl, OR$^{10}$, OH, NR$^{11}$R$^{12}$, S(O)$_x$R$^{13}$ (where x=0, 1 or 2), CONR$^{14}$R$^{15}$, NR$^{14}$COR$^{15}$, SO$_2$NR$^{14}$R$^{15}$, NR$^{14}$SO$_2$R$^{15}$, CN, nitro;

R$^5$ and R$^6$ independently represent a hydrogen atom, a C$_{1-6}$alkyl group, or an aryl, or a heteroaryl, the latter three of which may be optionally substituted by one or more substituents independently selected from halogen atoms, aryl, OR$^8$ and NR$^{14}$R$^{15}$, CONR$^{14}$R$^{15}$, NR$^{14}$COR$^{15}$, SO$_2$NR$^{14}$R$^{15}$, NR$^{14}$SO$_2$R$^{15}$; CN, nitro or R$^5$ and R$^6$ together with the nitrogen atom to which they are attached can form a 3-8 membered saturated heterocylic ring optionally containing one or more atoms selected from O, S(O)$_x$ where x=0, 1 or 2, NR$^{16}$, and itself optionally substituted by C$_{1-3}$ alkyl;

R$^7$ and R$^{13}$ independently represent a C$_1$-C$_6$, alkyl, an aryl or a heteroaryl group, all of which may be optionally substituted by halogen atoms;

R$^8$ represents a hydrogen atom, C(O)R$^9$, C$_1$-C$_6$ alkyl (optionally substituted by halogen atoms or aryl) an aryl or a heteroaryl group (optionally substituted by halogen);

each of $R^9$, $R^{10}$, $R^{11}$, $R^{12}$, $R^{14}$, $R^{15}$, independently represents a hydrogen atom, $C_1$-$C_6$ alkyl an aryl or a heteroaryl group (all of which may be optionally substituted by halogen atoms); and $R^{16}$ is hydrogen, $C_{1-4}$ alkyl, —$COC_1$-$C_4$ alkyl, $COYC_1$-$C_4$alkyl where Y is O or $NR^7$.

2. A compound according to claim 1 in which $R^1$ is hydrogen, halogen, heteroaryl, $CF_3$, alkyl, cyano, $CONR^5R^6$, $SO_2NR^5R^6$, $SO_2$alkyl, $NR^9SO_2R^4$, $NR^9COR^4$, $NR^9SO_2NR^5R^6$.

3. A compound according to claim 1 in which $R^1$ is hydrogen, chlorine, fluorine, $NHSO_2Me$, $NHSO_2Et$, $SO_2Me$, $CF_3$, $NHCOMe$, pyrazinyl, or $NHSO_2NMe_2$.

4. A compound according to claim 1 in which $R^2$ is $C_{1-6}$ alkyl.

5. A compound according to claim 4 in which $R^2$ is methyl.

6. A compound according to claim 1 which $R^3$ is phenyl substituted by one or more halogen atoms, $CONR^5R^6$, $SO_2NR^5R^6$, cyano or $SO_2R^4$ groups.

7. A compound according to claim 1 in which $R^3$ is phenyl substituted by chlorine or $SO_2Me$, CONHMe, CONHEt, CONHPr, $NH(CH_2)_3NH_2$ or cyano.

8. A compound according to claim 1 selected from:
3-(4-Chlorophenoxy)-5-fluoro-2-methyl-1H-indole-1-acetic acid;
5-Fluoro-2-methyl-3-[4-(methylsulfonyl)phenoxy]-1H-indole-1-acetic acid;
3-(4-Chlorophenoxy)-2-methyl-4-[(methylsulfonyl)amino]-1H-indole-1-acetic acid;
4-(Acetylamino)-3-(4-chlorophenoxy)-2-methyl-1H-indole-1-acetic acid;
3-(4-chlorophenoxy)-2-methyl-5-(methylsulfonyl)-1H-indole-1-acetic acid;
3-(4-chlorophenoxy)-2-methyl-5-(trifluoromethyl) 1H-indole-1-acetic acid;
3-(4-Chlorophenoxy)-2-methyl-5-[(methylsulfonyl)amino]-1H-indole-1-acetic acid;
3-(4-Chlorophenoxy)-5-[(ethylsulfonyl)amino]-2-methyl 1H-indole-1-acetic acid;
3-(4-Carboxyphenoxy)-5-fluoro-2-methyl-1H-indole-1-acetic acid;
5-Fluoro-2-methyl-3-[4-[(methylamino)carbonyl]phenoxy]-1H-indole-1-acetic acid;
3-[4-[(Ethylamino)carbonyl]phenoxy]-5-fluoro-2-methyl-1H-indole-1-acetic acid;
5-Fluoro-2-methyl-3-[4-[[(1-methylethyl)amino]carbonyl]phenoxy]-1H-indole-1-acetic acid;
3-(4-Carboxyphenoxy)-5-chloro-2-methyl-1H-indole-1-acetic acid;
5-Fluoro-3-[4-(methoxycarbonyl)phenoxy]-2-methyl-1H-indole-1-acetic acid;
5-Chloro-3-[4-(methoxycarbonyl)phenoxy]-2-methyl 1H-indole-1-acetic acid;
5-Chloro-2-methyl-3-[4-[(methylamino)carbonyl]phenoxy]-1H-indole-1-acetic acid;
5-Chloro-3-[4-[(ethylamino)carbonyl]phenoxy]-2-methyl-1H-indole-1-acetic acid;
Sodium 5-Chloro-2-methyl-3-[4-[[(1-methylethyl)amino]carbonyl]phenoxy]-1H-indole-1-acetate;
3-[4-[[(2-Aminoethyl)amino]carbonyl]phenoxy]-5-fluoro-2-methyl-1H-indole-1-acetic acid;
2,5-Dimethyl-3-[4-(methylsulfonyl)phenoxy]-1H-indole-1-acetic acid;
2-Methyl-3-[4-(methylsulfonyl)phenoxy]-5-(trifluoromethyl) 1H-indole-1-acetic acid;
5-Chloro-α,2-dimethyl-3-[4-(methylsulfonyl)phenoxy]-1H-indole-1-acetic acid;
5-Cyano-2-methyl-3-[4-(methylsulfonyl)phenoxy]-1H-indole-1-acetic acid;
3-(4-Chlorophenoxy)-4-[(ethylsulfonyl)amino]-2-methyl 1H-indole-1-acetic acid;
3-(4-Chlorophenoxy)-4-[[(dimethylamino)sulfonyl]amino]-2-methyl-1H-indole-1-acetic acid;
3-(4-Chlorophenoxy)-2-methyl-4-pyrazinyl-1H-indole-1-acetic acid;
3-(4-Chlorophenoxy)-2-methyl-4-[[(1-methylethyl)sulfonyl]amino]-1H-indole-1-acetic acid;
3-[4-[(Dimethylamino)sulfonyl]phenoxy]-5-fluoro-2-methyl-1H-indole-1-acetic acid;
3-[4-(Ethylsulfonyl)phenoxy]-5-fluoro-2-methyl 1H-indole-1-acetic acid;
3-[4-(Ethylsulfonyl)phenoxy]-2-methyl-5-(trifluoromethyl)-1H-indole-1-acetic acid;
3-(4Cyanophenoxy)-2-methyl-5-(trifluoromethyl)-1H-indole-1-acetic acid;
3-(4-Cyanophenoxy)-5-fluoro-2-methyl 1H-indole-1-acetic acid;
and pharmaceutically acceptable salts thereof.

9. A method of treating asthma or rhinitis, which comprises administering to a patient a therapeutically effective amount of a compound of formula (I), or a pharmaceutically acceptable salt as defined in claim 1.

10. A process for the preparation of a compound of formula (I) claim 1, which comprises reaction of a compound of formula (II):

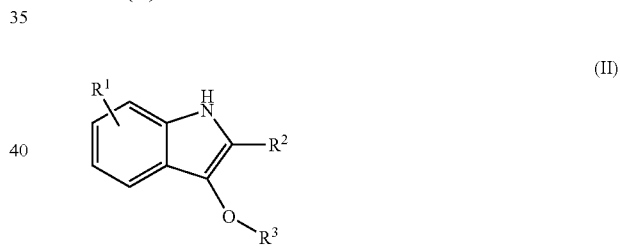

(II)

in which $R^1$, $R^2$ and $R^3$ are as defined in formula (I) or are protected derivatives thereof, with a compound of formula (IIA):

L-$CH_2CO_2R^{17}$ (IIA)

where $R^{17}$ is an ester forming group and L is a leaving group in the presence of a base, and optionally thereafter in any order:
removing any protecting group
hydrolysing the ester group $R^{17}$ to the corresponding acid
forming a pharmaceutically acceptable salt.

11. A pharmaceutical composition comprising a compound of formula (I) or a pharmaceutically acceptable salt thereof as claimed in claim 1 in association with a pharmaceutically acceptable adjuvant, diluent or carrier.

* * * * *

UNITED STATES PATENT AND TRADEMARK OFFICE
CERTIFICATE OF CORRECTION

| | |
|---|---|
| PATENT NO. | : 7,709,521 B2 |
| APPLICATION NO. | : 10/568889 |
| DATED | : May 4, 2010 |
| INVENTOR(S) | : Roger Victor Bonnert et al. |

It is certified that error appears in the above-identified patent and that said Letters Patent is hereby corrected as shown below:

Column 36, line 20, "S(O)xR$^4$" should read -- S(O)$_x$R$^4$ --.

Column 37, line 1, "R$^9$R$^{10}$" should read -- R$^9$, R$^{10}$, --.

Column 37, line 2, "alkyl" should read -- alkyl, --.

Column 38, line 19, "methyl 1H" should read -- methyl-1H --.

Column 38, line 23, "(4Cyanophenoxy)" should read -- (4-Cyanophenoxy) --.

Signed and Sealed this

Sixteenth Day of November, 2010

David J. Kappos
*Director of the United States Patent and Trademark Office*